US009493551B2

(12) United States Patent
Springhorn et al.

(10) Patent No.: US 9,493,551 B2
(45) Date of Patent: Nov. 15, 2016

(54) ANTIBODIES CONTAINING THERAPEUTIC TPO/EPO MIMETIC PEPTIDES

(75) Inventors: Jeremy P. Springhorn, Guilford, CT (US); David Gies, Southbury, CT (US)

(73) Assignee: Alexion Pharmaceuticals, Inc., New Haven, CT (US)

(*) Notice: Subject to any disclaimer, the term of this patent is extended or adjusted under 35 U.S.C. 154(b) by 1192 days.

(21) Appl. No.: 13/202,932

(22) PCT Filed: Feb. 18, 2010

(86) PCT No.: PCT/US2010/024546
§ 371 (c)(1),
(2), (4) Date: Nov. 7, 2011

(87) PCT Pub. No.: WO2010/099019
PCT Pub. Date: Sep. 2, 2010

(65) Prior Publication Data
US 2012/0070434 A1 Mar. 22, 2012

Related U.S. Application Data

(60) Provisional application No. 61/208,487, filed on Feb. 24, 2009.

(51) Int. Cl.
| | |
|---|---|
| *C07K 16/18* | (2006.01) |
| *C07K 7/08* | (2006.01) |
| *C07K 14/52* | (2006.01) |
| *A61K 38/00* | (2006.01) |
| *G01N 33/86* | (2006.01) |
| *A61K 39/00* | (2006.01) |

(52) U.S. Cl.
CPC ............. *C07K 16/18* (2013.01); *G01N 33/86* (2013.01); *A61K 2039/505* (2013.01); *C07K 2317/24* (2013.01); *C07K 2317/565* (2013.01); *C07K 2319/00* (2013.01)

(58) Field of Classification Search
CPC ........... C07K 16/18; C07K 2317/565; C07K 2317/24; C07K 2318/00; C07K 7/08; A61K 2039/505; A61K 2039/00; A61K 38/00
See application file for complete search history.

(56) References Cited

U.S. PATENT DOCUMENTS

| | | | |
|---|---|---|---|
| 6,083,913 A | 7/2000 | Dower et al. | |
| 7,091,396 B1 | 8/2006 | Simon et al. | |
| 2003/0049683 A1* | 3/2003 | Bowdish et al. | 435/7.1 |
| 2004/0253242 A1* | 12/2004 | Bowdish | C07K 14/505 424/145.1 |
| 2006/0127404 A1* | 6/2006 | Huang et al. | 424/155.1 |

FOREIGN PATENT DOCUMENTS

| | | |
|---|---|---|
| WO | WO 01/10912 A1 | 2/2001 |
| WO | WO 02/46238 A2 | 6/2002 |
| WO | WO 2004/050017 A2 | 6/2004 |
| WO | WO 2005/021579 A2 | 3/2005 |
| WO | WO 2005/032460 A2 | 4/2005 |
| WO | WO 2006/036834 A2 | 4/2006 |
| WO | 2007/048022 A2 | 4/2007 |
| WO | WO 2007/085084 A1 | 8/2007 |
| WO | WO 2007115148 | * 10/2007 |

OTHER PUBLICATIONS

Colman et al., Research in Immunology 145(1):33-35, 1994.*
Lederman et al., Molecular Immunology 28:1171-1181, 1991.*
Rudikoff et al., Proc. Natl. Acad. Sci. USA vol. 79: 1979-1983, 1982.*
Wu et al., J. Mol. Biol. 294: 151-162, 1999.*
Tunheim et al., International Immunology 20(3): 295-306, 2008.*
Dolezal et al., "*Escherichia coli* expression of a bifunctional Fab-peptide epitope reagent for the rapid diagnosis of HIV-1 and HIV-2," Immunotechnology, vol. 1(3): 197-209 (1995).
Flobakk et al., "Processing of an Antigenic Sequence from IgG Constant Domains for presentation by MHC Class II," The Journal of Immunology, vol. 181(10): 7062-7072 (2008).
Metheringham et al., "Antibodies designed as effective cancer vaccines," MABS, vol. 1(1): 71-85 (2009).
Supplementary European Search Report dated Sep. 10, 2013 for EP 10 74 6652.
Bussel et al., "AMG 531, a Thrombopoiesis-Stimulating Protein, for Chronic ITP," The New England Journal of Medicine, vol. 355(16), pp. 1672-1681 (2006).
Faber, et al., "Three-dimensional structure of a human Fab with high affinity for tetanus toxoid," Immunotechnology, 3:253-270, (1998).

* cited by examiner

*Primary Examiner* — Phuong Huynh
(74) *Attorney, Agent, or Firm* — Nelson Mullins Riley & Scarborough LLP; Jane E. Remillard, Esq.; Christopher L. Frank

(57) ABSTRACT

The present disclosure features therapeutic antibodies (e.g., TPO mimetic antibodies) and therapeutically-active fragments thereof as well as methods for preparing and using the antibodies and fragments. For example, the therapeutic antibodies and their fragments are useful in a variety of diagnostic and/or therapeutic applications such as methods for increasing platelet levels in a subject.

11 Claims, 4 Drawing Sheets

ANTIBODIES CONTAINING THERAPEUTIC TPO/EPO MIMETIC PEPTIDES

RELATED APPLICATIONS

This application is a national stage filing under 35 U.S.C. 371 of International Application No. PCT/US2010/024546, filed Feb. 18, 2010, which claims the benefit of the filing date under 35 U.S.C. 119(e) to U.S. Provisional Application Ser. No. 61/208,487, filed Feb. 24, 2009, the entire contents of which is hereby incorporated by reference. International Application PCT/US/2010/024546 was published under PCT Article 21(2) in English.

SEQUENCE LISTING

The instant application contains a Sequence Listing which has been submitted via EFS-Web and is hereby incorporated by reference in its entirety. Said ASCII copy, created on Nov. 7, 2011, is named ALXN_146_301_Sequence.txt, and is 19,526 bytes in size.

TECHNICAL FIELD

The field of the invention is medicine, immunology, molecular biology, and protein chemistry.

BACKGROUND

Thrombocytopenia is associated with a variety of diseases and is characterized by abnormally low platelet counts in the blood often due to platelet underproduction, platelet sequestration, production of defective platelets, or increased platelet destruction. Symptoms of thrombocytopenia include, e.g., malaise, bruising (e.g., purpura), and bleeding (e.g., from the nose or gums). One example of a thrombocytopenia-associated disease is thrombotic thrombocytopenic purpura (TTP), which is a disorder characterized by extensive microscopic blood clot formation (thrombi) in small blood vessels throughout the body. If left untreated, a patient's condition can rapidly deteriorate to include severe neurological defects (e.g., stupor or coma), renal failure, stroke, and cardiac arrest. The mortality rate for untreated TTP is greater than 90%.

Thrombocytopenia-associated diseases can also result from exposure to radiation (e.g., a radiotherapy regimen), cancers, the administration of certain compounds (e.g., cytotoxic drugs), and immune responses to certain vaccines.

Thrombopoietin (TPO) is a glycosylated growth factor that stimulates the production and differentiation of megakaryocytes, the bone marrow cells that give rise to large numbers of platelets. (See, e.g., Kaushansky (2006) *N. Engl. J. Med.* 354(19):2034-45.) TPO binds to the c-Mpl receptor expressed on megakaryocytic progenitor cells to thus stimulate proliferation and differentiation of the cells into platelets. Paradoxically, treatment of patients with recombinant human TPO resulted in the generation of anti-TPO neutralizing antibodies that bound to and interfered with the activity of the patient's naturally occurring TPO. (See, e.g., Kuter and Begley (2002) *Blood* 100:3457-3469; Li et al. (2001) *Blood* 98:3241-3248; and Vadhan-Raj et al. (2000) *Ann Intern Med* 132:364-368.) Thus, there is a need for new and better treatments for patients with thrombocytopenia-associated diseases.

SUMMARY

The disclosure relates to therapeutically-active, recombinant antibodies that contain therapeutic peptides (hereinafter these antibodies are referred to as "therapeutic antibodies"). In some embodiments, the antibodies contain thrombopoietin (TPO) mimetic peptides (hereinafter these antibodies are referred to as "TPO mimetic antibodies") in accordance with the disclosure. The disclosure also relates to therapeutically-active fragments of the therapeutic antibodies (e.g., therapeutically-active fragments of the TPO mimetic antibodies). The therapeutic antibodies and their fragments can be used, e.g., in a variety of diagnostic and/or therapeutic applications. For example, as described in the working examples, the TPO mimetic antibodies and/or their fragments can be used to treat a subject in need of increased platelet production, e.g., a subject exposed to radiation (e.g., a cancer patient undergoing radiotherapy) or to other agents that deplete bone marrow, decrease platelet production, and/or increase platelet destruction. The TPO mimetic antibodies and/or fragments can also be used to treat a subject having a disorder related to insufficient platelet levels (a thrombocytopenia) such as any of these disorders described herein or known in the art.

The therapeutic antibodies, and therapeutically-active fragments thereof, described herein have a number of advantages as compared to the corresponding isolated therapeutic peptides. First, the antibodies have an increased serum half-life. Second, the conformation of the active region of the therapeutic peptide within the antibody scaffold can be stabilized, rendering it more active and specific with respect to its binding to the target, as compared to isolated therapeutic peptides. In addition, the TPO mimetic antibodies and fragments described herein have a number of additional advantages as compared to their isolated native TPO peptide counterparts. For example, when administered to a mammalian subject (e.g., a human subject), the TPO mimetic antibodies, or therapeutically-active fragments thereof, substantially reduce the likelihood that a detrimental immune response will be produced toward native TPO. This is in contrast to treatment using recombinant forms of native TPO protein that often result in generation of TPO neutralizing antibodies in patients, which antibodies interfere with the activity of the patient's naturally occurring TPO. See, e.g., Kuter and Begley (2002) *Blood* 100:3457-3469; Li et al. (2001) *Blood* 98:3241-3248; and Vadhan-Raj et al. (2000) *Ann Intern Med* 132:364-368. Yet another advantage of the TPO mimetic antibodies (and therapeutically-active fragments) described herein is that a single dose of the TPO mimetic antibodies is as effective, or more effective, in elevating platelet levels in a subject than a multi-dose regimen.

Many of the advantages of the therapeutic antibodies described herein stem from the unique position(s) of the therapeutic peptides within the antibody scaffold. As detailed herein and exemplified in the working Examples, the inventors have developed therapeutic antibodies containing a therapeutic peptide that is incorporated at a unique position within the light chain polypeptide constant region and/or a therapeutic peptide that is incorporated at a unique position within the heavy chain polypeptide constant region. For example, the inventors have determined that incorporating a therapeutic peptide at or near the hinge region of the heavy chain polypeptide results in a therapeutic antibody having many of the advantages described herein. Similarly, by incorporating a therapeutic peptide at a position in the light chain constant region that is structurally permissive to allow for the therapeutic peptide to be presented at the central cleft of the antibody (e.g., a β-turn region of the light chain polypeptide constant region or at the carboxy-terminus of the light chain constant region), a therapeutic antibody is produced that has many of the advantages described herein. The "central cleft" of an antibody, as used herein, refers to the region of a whole antibody where the two "arms" of the antibody meet. That is, all whole immunoglobulin (Ig) molecules consist of four protein chains (two heavy chain polypeptides and two light chain polypeptides) that adopt a three-dimensional structure shaped like a capital letter "Y," which is linked together by disulphide bonds. The "arms" of the "Y" structure contain the variable regions of the antibody and the central cleft region is located at the junction between the two arms of the "Y" structure.

Accordingly, in one aspect, the disclosure features a therapeutic antibody, or a therapeutically-active fragment of the antibody, wherein the antibody or fragment comprises at least two therapeutic peptides and wherein at least one of the therapeutic peptides is incorporated into the constant region of a light chain polypeptide at a position that is structurally permissive to allow for the therapeutic peptide to be presented at the central cleft of the antibody. The therapeutic antibody, or fragment thereof, can also contain a heavy chain polypeptide that contains at least one of the therapeutic peptides. The at least one therapeutic peptide is incorporated into the hinge region as follows: (a) into the hinge region of the heavy chain polypeptide; (b) at the junction between the amino-terminus of the hinge region and the region of the heavy chain polypeptide that is upstream to the hinge region; (c) at the junction between the carboxy-terminus of the hinge region and the region of the heavy chain polypeptide that is downstream of the hinge region; or (d) at a location starting within fewer than 20 amino acids upstream of the amino-terminus, or fewer than 20 amino acids downstream of the carboxy-terminus, of the hinge region of the heavy chain polypeptide.

In another aspect, the disclosure features a therapeutic antibody, or a therapeutically-active fragment of the antibody, wherein the antibody or fragment comprises at least two therapeutic peptides and wherein a heavy chain polypeptide of the antibody comprises at least one of the therapeutic peptides incorporated into the heavy chain as follows: (a) into the hinge region of the heavy chain polypeptide; (b) at the junction between the amino-terminus of the hinge region and the region of the heavy chain polypeptide that is upstream to the hinge region; (c) at the junction between the carboxy-terminus of the hinge region and the region of the heavy chain polypeptide that is downstream of the hinge region; or (d) at a location starting within fewer than 20 amino acids upstream of the amino-terminus, or fewer than 20 amino acids downstream of the carboxy-terminus, of the hinge region of the heavy chain polypeptide. The therapeutic antibody, or therapeutically-active fragment thereof, can also contain a light chain polypeptide in which the constant region of a light chain polypeptide comprises at least one of the therapeutic peptides. The therapeutic peptide (e.g., the TPO mimetic peptide) is incorporated into the constant region of the light chain polypeptide at a position that is structurally permissive to allow for the therapeutic peptide to be presented at the central cleft of the antibody.

In some embodiments of any of the therapeutic antibodies or fragments thereof described herein, the therapeutic peptide can be incorporated as an insertion and/or replacement within a β-turn region of the light chain polypeptide constant region. In some embodiments of any of the therapeutic antibodies or fragments thereof described herein, the therapeutic peptide can be incorporated as an addition to the carboxy-terminus of the light chain polypeptide. In some embodiments, the therapeutic peptide can be incorporated as an insertion to and/or replacement of a region of the light chain polypeptide constant region that is downstream from the final β-sheet structure in the polypeptide.

In some embodiments of any of the therapeutic antibodies or therapeutically-active fragments thereof, the entire hinge region of the heavy chain is replaced with a therapeutic peptide.

In some embodiments of any of the therapeutic antibodies or therapeutically-active fragments thereof, the carboxy-terminus of a light chain polypeptide comprises at least one of the therapeutic peptides and a heavy chain polypeptide comprises at least one of the therapeutic peptides.

In some embodiments of any of the therapeutic antibodies or therapeutically-active fragments thereof, the antibody or fragment comprises at least three (e.g., at least four, five, six, seven, eight, nine, 10, 11, 12, or 15 or more) therapeutic peptides. In some embodiments of any of the therapeutic antibodies or therapeutically-active fragments thereof, at least two of the therapeutic peptides are identical. In some embodiments, at least two of the therapeutic peptides are different from one another. For example, the at least two different therapeutic peptides can have a different amino acid sequence, but the same type of therapeutic activity (e.g., two TPO mimetics having different amino acid sequences) or the at least two different therapeutic peptides can have a different amino acid sequence and a different therapeutic activity (e.g., a TPO mimetic and an EPO mimetic). In some embodiments of any of the therapeutic antibodies or therapeutically-active fragments thereof, all of the therapeutic peptides are identical. In some embodiments, all of the therapeutic peptides are different from one another (e.g., one or both of a different amino acid sequence and a different therapeutic activity).

In some embodiments of any of the therapeutic antibodies or therapeutically-active fragments thereof, at least one antigen combining site of a therapeutic antibody or therapeutically-active fragment thereof retains the ability to bind to an antigen. In some embodiments, at least two antigen combining sites of a therapeutic antibody or therapeutically-active fragment thereof retain the ability to bind to an antigen.

In some embodiments, any of the therapeutic antibodies or therapeutically-active fragments thereof can include a spacer amino acid sequence that is amino-terminal to at least one therapeutic peptide and/or a spacer amino acid sequence that is carboxy-terminal to at least one therapeutic peptide. In some embodiments, a spacer amino acid sequence can be present at both the amino-terminal and carboxy-terminal end of a therapeutic peptide. The two spacers can have the same amino acid sequence or a different amino acid sequence.

In some embodiments of any of the therapeutic antibodies or therapeutically-active fragments thereof, at least one therapeutic peptide is an antagonist peptide. In some embodiments of any of the therapeutic antibodies or therapeutically-active fragments thereof, at least one therapeutic peptide is an agonist peptide. In some embodiments of any of the therapeutic antibodies or therapeutically-active fragments thereof, at least one therapeutic peptide is a peptidomimetic (e.g., a TPO mimetic or an EPO mimetic). In some embodiments of any of the therapeutic antibodies or therapeutically-active fragments thereof all of the therapeutic peptides are a TPO mimetic (e.g., a TPO mimetic containing, or consisting of, the amino acid sequence depicted in SEQ ID NO:1 or SEQ ID NO:2).

In some embodiments of any of the therapeutic antibodies or therapeutically-active fragments thereof, the therapeutic antibody can contain a light chain polypeptide comprising the amino acid sequence depicted in SEQ ID NO:10 and/or a heavy chain polypeptide comprising the amino acid sequence depicted in SEQ ID NO:12. In some embodiments of any of the therapeutic antibodies or therapeutically-active fragments thereof, the antibody contains, or consists of, a light chain polypeptide comprising the amino acid sequence depicted in SEQ ID NO:10 and a heavy chain polypeptide comprising the amino acid sequence depicted in SEQ ID NO:12. In some embodiments of any of the therapeutic antibodies or therapeutically-active fragments thereof, the antibody consists of light chain polypeptides comprising the amino acid sequence depicted in SEQ ID NO:10 and heavy chain polypeptides comprising the amino acid sequence depicted in SEQ ID NO:12.

In some embodiments of any of the therapeutic antibodies or therapeutically-active fragments thereof, the antibody can be a monoclonal antibody, a humanized antibody, a chimerized antibody, a chimeric antibody, a deimmunized human antibody, a fully human antibody, or an F(ab')$_2$ fragment.

In some embodiments of any of the therapeutic antibodies or therapeutically-active fragments thereof, the therapeutically-active fragment can be selected from the group consisting of an Fd fragment, an Fab fragment, and an Fab' fragment, wherein the therapeutically-active fragment contains at least two of the therapeutic peptides; and at least part of a hinge region of a heavy chain polypeptide or at least part of the carboxy-terminus of a light chain polypeptide.

In some embodiments of any of the therapeutic antibodies or therapeutically-active fragments thereof, the antibody or therapeutically-active fragment contains a heterologous moiety.

In some embodiments, any of the therapeutically-active fragments described herein include at least part, or all, of the variable region of a light chain polypeptide and/or a heavy chain polypeptide of an antibody. Part of a variable region includes at least two (e.g., at least three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100) amino acids of a light chain polypeptide and/or a heavy chain polypeptide. At least part of a variable region can include one or more of a light chain (LC) polypeptide or heavy chain (HC) polypeptide CDR (e.g., LC-CDR1, LC-CDR2, LC-CDR3, HC-CDR1, HC-CDR2, or HC-CDR3), framework region (FR) (e.g., LC-FR1, LC-FR2, LC-FR3, LC-FR4, HC-FR1, HC-FR2, HC-FR3, or HC-FR4), or any combination of any of the foregoing. In some embodiments, the therapeutically-active fragment is not an Fc fragment of an antibody.

In another aspect, the disclosure features a composition of any of the therapeutic antibodies or therapeutically-active fragments thereof and a pharmaceutically acceptable carrier. For example, in some embodiments the compositions can contain any of the TPO mimetic antibodies described herein.

In some embodiments, any of the compositions described herein can be formulated for use as a single dose. In some embodiments, any of the compositions described herein can be formulated for use in multiple doses.

In some embodiments, any of the compositions described herein can also contain at least one active agent for reducing the side-effects of radiation exposure or for reducing the side-effects of chemotherapy. The at least one active agent can be selected from the group consisting of an antibiotic, an anesthetic, an antiemetic, a steroid, a chelating agent, and a diuretic.

In some embodiments, any of the compositions described herein can also include at least one additional active agent for increasing platelet production in a subject. The at least one additional active agent can be, e.g., eltrombopag, oprelvekin, romiplostim, pegfilgrastim, an erythropoietin-stimulating agent (ESA), or any other suitable agent described herein or known in the art.

In yet another aspect, the disclosure features a method for increasing platelet production in a subject. The method includes the step of administering to a subject in need thereof a therapeutically-effective amount of a composition comprising any of the TPO mimetic antibodies or therapeutically-active fragments thereof described herein.

In another aspect the disclosure features a method for increasing platelet production in a subject, which method includes administering to a subject in need thereof a composition comprising a therapeutically-effective amount of any of the TPO mimetic antibodies or therapeutically-active fragments thereof described herein.

In some embodiments of any of the methods described herein, the subject is a mammal, e.g., a human or a non-human primate. In some embodiments of any of the methods described herein, the subject is a non-human mammal.

In some embodiments of any of the methods described herein, the subject has a disorder related to insufficient platelet counts. The disorder can be, e.g., any one of Bernard-Soulier syndrome, idiopathic thrombocytopenic purpura, Wiskott-Aldrich syndrome, hypersplenism, thrombotic microangiopathies, disseminated intravascular coagulation, heparin-induced thrombocytopenia (HIT), von Willebrand disease, variant von Willebrand disease, thrombocytopenia resulting from HIV infection, thrombocytopenia resulting from chronic liver disease, or Glanzmann's thrombasthenia. In some embodiments, the disorder can result from the treatment of a subject for a viral infection, a cancer, or an inflammatory disorder. For example, the disorder can be the result of a cytotoxic drug therapy (e.g., drug-induced platelet insufficiency). In some embodiments, the disorder can result from administration to a subject of a radiotherapy regimen.

In some embodiments of any of the methods described herein, the subject can have a cancer such as, but not limited to, lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

In some embodiments of any of the methods described herein, the platelet insufficiency is induced by a chemotherapeutic drug.

In some embodiments of any of the methods described herein, the subject has been administered, or will be administered, a chemotherapy regimen or a radiotherapy regimen. The chemotherapy regimen can include administering to the subject one or more cytotoxic agents selected from the group consisting of cyclophosphamide, taxol, methotrexate, nitrogen mustard, azathioprine, chlorambucil, fluorouracil, cisplatin, nocodazole, hydroxyurea, vincristine, vinblastine, etopiside, doxorubicin, bleomycin, carboplatin, gemcitabine, paclitaxel, topotecan, and thioguanine. The radiotherapy regimen can include X-ray or gamma-irradiation. The radiotherapy regimen can include administering to the subject a radioactive agent. In some embodiments, the composition can be administered to the subject prior to the chemotherapy regimen or the radiotherapy regimen. In some embodiments, the composition can be administered to the subject during or following the chemotherapy regimen or the radiotherapy regimen.

In some embodiments of any of the methods described herein, the composition can be administered to the subject intravenously, subcutaneously, intraperitoneally, or intramuscularly. In some embodiments of any of the methods described herein, the composition is administered to the subject as a single dose or as more than one (e.g., two, three, four, five, six, seven, eight, nine, 10, or 15 or more) dose(s) of the composition.

In some embodiments of any of the methods described herein, the composition can be administered to the subject: (i) prior to and (ii) during or following the chemotherapy or the radiotherapy regimen.

In some embodiments of any of the methods described herein, the chemotherapy or radiotherapy regimen can be (i) more potent or (ii) administered more frequently to a subject than would be safely possible in the absence of administering the composition.

In some embodiments, any of the methods described herein can also include administering to the subject at least one additional agent for reducing the side-effects of a chemotherapy regimen or a radiotherapy regimen. The at least one agent can be selected from the group consisting of an antibiotic, an anesthetic, an antiemetic, and a steroid such as an androstenediol. In some embodiments, any of the methods described herein can also include administering to the subject at least one additional agent for increasing platelet production. The at least one additional agent for increasing platelet production can be one selected from the group consisting of eltrombopag, oprelvekin, romiplostim, pegfilgrastim, and an ESA.

In some embodiments, any of the methods described herein can also include, after administering the composition, monitoring the subject for an increase in platelet levels.

In yet another aspect, the disclosure features a method for increasing platelet production in a subject, which method includes administering to a subject in need thereof a single dose of a platelet production-increasing amount of a TPO mimetic antibody, or a therapeutically-active fragment thereof, described herein. The disclosure also features a method for treating a subject for radiation exposure or a platelet level-decreasing chemotherapy regimen. The method includes administering to a subject a single dose of a platelet production-increasing amount of a TPO mimetic antibody, or a therapeutically-active fragment thereof, described herein. The subject can be one who has undergone, who is likely to undergo, or is scheduled to undergo, a chemotherapy or radiotherapy regimen. The subject can be one who has been, who is likely to be, or is scheduled to be, exposed to radiation.

In yet another aspect, the disclosure features a method for increasing platelet production in a subject, which method includes administering to a subject in need thereof multiple (e.g., at least two, three, four, five, six, seven, eight, nine, 10, 11, or 12 or more) doses of a platelet production-increasing amount of a TPO mimetic antibody, or a therapeutically-active fragment thereof, described herein. The disclosure also features a method for treating a subject for radiation exposure or a platelet level-decreasing chemotherapy regimen. The method includes administering to a subject multiple doses of a platelet production-increasing amount of a TPO mimetic antibody, or a therapeutically-active fragment thereof, described herein. The subject can be one who has undergone, who is likely to undergo, or is scheduled to undergo, a chemotherapy or radiotherapy regimen. The subject can be one who has been, who is likely to be, or is scheduled to be, exposed to radiation.

In another aspect, the disclosure features a nucleic acid encoding a polypeptide containing at least one (e.g., at least two, three, four, five, six, or eight) TPO mimetic peptide(s), wherein the amino acid sequence of the polypeptide is at least 80 (e.g., at least 81, 82, 83, 84, 85, 86, 87, 88, 89, 90, 91, 92, 93, 94, 95, 96, 97, 98, 99, or 100) % identical to the amino acid sequence depicted in SEQ ID NO:10 or SEQ ID NO:12. In some embodiments, the nucleic acid encodes a polypeptide having an amino acid sequence that is at least 80% identical to amino acids 1-214 of SEQ ID NO:10 or at least 80% identical to amino acids 1-218 of SEQ ID NO:10, wherein amino acids 219-232 of SEQ ID NO:10 are 100% identical between the amino acid sequence and SEQ ID NO:10. In some embodiments, the nucleic acid encodes a polypeptide having an amino acid sequence that is at least 80% identical to amino acids 1-234 of SEQ ID NO:12 and at least 80% identical to amino acids 249-461 of SEQ ID NO:12, wherein amino acids 235-248 of SEQ ID NO:12 are 100% identical between the amino acid sequence and SEQ ID NO:12. In some embodiments, the nucleic acid encodes an amino acid sequence that is at least 80% identical to amino acids 1-232 of SEQ ID NO:12 and at least 80% identical to amino acids 251-461 of SEQ ID NO:12, wherein amino acids 235-248 of SEQ ID NO:12 are 100% identical between the amino acid sequence and SEQ ID NO:12.

Percent (%) amino acid sequence or nucleic acid sequence identity is defined as the percentage of amino acids, or nucleic acids, in a candidate sequence that are identical to the amino acids or nucleic acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2, or Megalign (DNASTAR) software. Appropriate parameters for measuring alignment, including any algorithms needed to achieve maximal alignment over the full-length of the sequences being compared can be determined by known methods.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for increasing platelet production in a subject, will be apparent from the following description, the examples, and from the claims.

Figure 1:
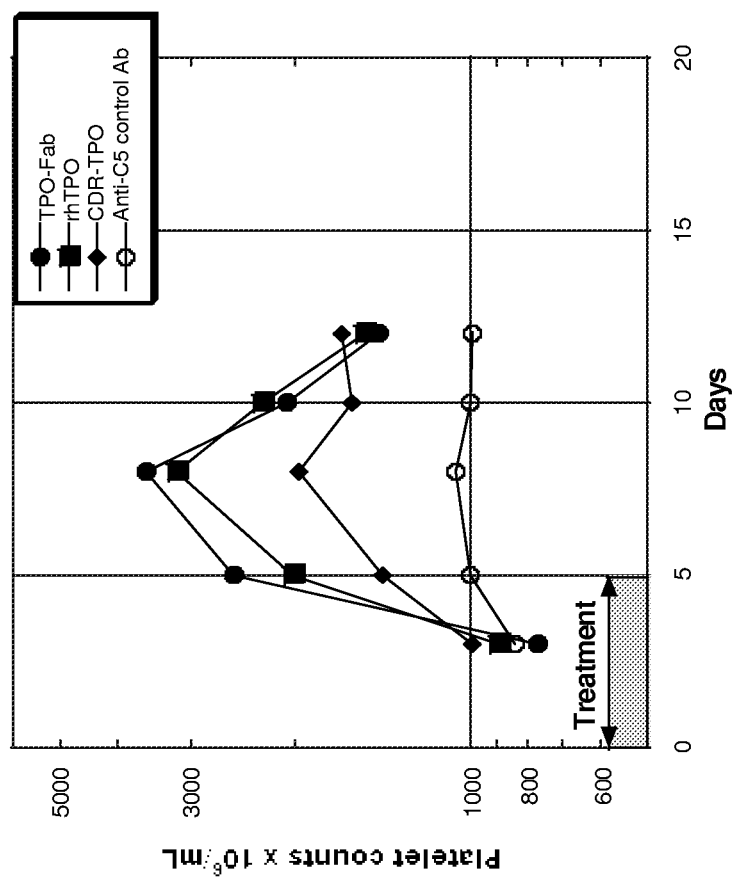
FIG. 1 is a line graph depicting the effect of a multi-dose regimen of recombinant human TPO, and several TPO mimetic compositions, on platelet levels in mice. The Y-axis represents platelet counts in units of $10^6$/mL. The X-axis depicts the days following the start of the treatment regimen. As indicated by the double-headed arrow, treatment proceeded for 5 days. The black circles represent mice treated with a $F(ab')_2$ antibody fragment containing a TPO mimetic in the CDR3 region of the heavy chain and the CDR2 region of the light chain of the $F(ab')_2$ antibody. The open circles represent mice treated with an anti-complement component C5 antibody (5G1.1) that did not contain a TPO mimetic. The black squares represent mice treated with recombinant human TPO and the black diamonds represent mice treated with an anti-complement component C5 antibody (5G1.1) that contains a TPO mimetic in the CDR3 region. The anti-C5 antibody containing the TPO mimetic does not bind to C5. The heavy chain constant region of the anti-C5 antibodies is an IgG2/IgG4 constant region fusion.

FIG. 2 is a line graph depicting the effect of a multi-dose regimen of TPO mimetic antibodies on platelet levels in mice. The Y-axis represents platelet counts in units of $10^6$/mL. The X-axis depicts the days following the start of the treatment regimen. As indicated by the double-headed arrow, treatment proceeded for 5 days. The black diamonds represent mice treated with an anti-complement component C5 antibody (5G1.1) that contains a TPO mimetic in the CDR3 region of the heavy chain. The anti-C5 antibody containing the TPO mimetic does not bind to C5 and the heavy chain constant region of the anti-C5 antibody is an IgG2/IgG4 constant region fusion. The open squares represent mice treated with an anti-anthrax antibody that does not contain a TPO mimetic and has an IgG1 isotype constant region. The black triangles (right angle at bottom left) represent mice treated with an anti-anthrax antibody in which each of the light chain polypeptides contains a TPO mimetic peptide at its carboxy-terminus. The black triangles (right angle at bottom right) represent mice treated with an anti-anthrax antibody in which each of the heavy chain polypeptides contains a TPO mimetic near the hinge region. The black squares represent mice treated with an anti-anthrax antibody in which each of the light and heavy chain polypeptides contains a TPO mimetic peptide. Each of the anti-anthrax antibodies containing a TPO mimetic also contains an IgG2/IgG4 fusion heavy chain constant region.

FIG. 3 is a line graph depicting the effect of a single dose regimen of TPO mimetic antibodies on platelet levels in mice. The Y-axis represents platelet counts in units of $10^6$/mL. The X-axis depicts the days following the start of the treatment regimen. The filled squares represent mice treated with an anti-complement component C5 antibody (5G1.1) that contains a TPO mimetic in the CDR3 region. The anti-C5 antibody containing the TPO mimetic does not bind to C5. Each of the anti-C5 antibodies containing a TPO mimetic also contains an IgG2/IgG4 fusion heavy chain constant region. The asterisks represent mice treated with an anti-anthrax antibody that does not contain a TPO mimetic. The anti-anthrax antibody contains an IgG1 isotype heavy chain constant region. The filled triangles represent mice treated with an anti-anthrax antibody in which each of the light chain polypeptides contains a TPO mimetic peptide. The open triangles represent mice treated with an anti-anthrax antibody in which each of the light and heavy chain polypeptides contains a TPO mimetic peptide. The anti-anthrax antibody contains an IgG2/IgG4 fusion heavy chain constant region. The diamonds represent mice treated with an anti-anthrax antibody that does not contain a TPO mimetic, wherein the heavy chain constant region is an IgG2/IgG4 constant region.

FIG. 4 is a line graph depicting the effect of the CDR-TPO antibody on platelet levels following myelosuppressive therapy. The Y-axis represents platelet counts in units of $10^6$/mL. The X-axis depicts the days following the start of the treatment regimen. The filled circles represent mice treated with mitomycin C (MMC) and an anti-C5 antibody (5G1.1) that does not contain a TPO mimetic. The filled squares represent mice treated with MMC and the CDR-TPO antibody (the anti-C5 antibody (5G1.1) containing a TPO mimetic inserted into CDR3). The anti-C5 antibody containing the TPO mimetic does not bind to C5. The filled diamonds represent mice that were not treated with antibody or MMC. Each of the anti-C5 antibodies containing a TPO mimetic also contains an IgG2/IgG4 fusion heavy chain constant region.

DETAILED DESCRIPTION

The present disclosure features therapeutic antibodies (e.g., TPO mimetic antibodies) and therapeutically-active fragments thereof as well as methods for preparing and using the antibodies and fragments. While in no way intended to be limiting, exemplary antibodies and fragments, conjugates, pharmaceutical compositions and formulations, and methods for using any of the foregoing are elaborated on below and are exemplified in the working Examples.

Therapeutic Antibodies and Therapeutically-Active Fragments Thereof

The therapeutic antibodies (e.g., TPO mimetic antibodies) described herein contain at least two (e.g., two, three, four, five, six, seven, eight, nine, or 10 or more) therapeutic peptides (e.g., TPO mimetic peptides), wherein one or both of: (i) a light chain polypeptide of the antibody comprises at least one of the therapeutic peptides (e.g., a TPO mimetic peptide); and (ii) a heavy chain polypeptide of the antibody comprises at least one of the therapeutic peptides (e.g., a TPO mimetic peptide). The at least one therapeutic peptide (e.g., the TPO mimetic peptide) is incorporated into the heavy chain as follows: (a) into the hinge region itself; (b) at the junction between the amino-terminus of the hinge region and the upstream region of the heavy chain; (c) at the junction between the carboxy-terminus of the hinge region and the downstream region of the heavy chain; or (d) at a location starting within fewer than 20 (e.g., fewer than 19, 18, 17, 16, 15, 14, 13, 12, 11, 10, nine, eight, seven, six, five, four, three, two, or one) amino acids upstream from the amino-terminus, or fewer than 20 (e.g., fewer than 19, 18, 17, 16, 15, 14, 13, 12, 11, 10, nine, eight, seven, six, five, four, three, two, or one) amino acids downstream of the carboxy-terminus, of the hinge region.

In accordance with the disclosure, the at least one therapeutic peptide (e.g., the TPO mimetic peptide) is incorporated into the constant region of a light chain polypeptide at a position that is structurally permissive to allow for the therapeutic peptide to be presented at the central cleft of the antibody. As used herein, a region or position that is "structurally permissive," in the context of a light chain polypeptide constant region, refers to a region or position within the light chain constant region that (1) can tolerate insertion, replacement, and/or addition of a therapeutic peptide without substantially affecting the three-dimensional structure of the constant region and (2) allows the therapeutic peptide to be presented at the central cleft of the antibody without affecting the therapeutic activity of the therapeutic peptide. For example, the therapeutic peptide can be incorporated as: (a) an addition to the carboxy-terminus of the constant region of the light chain polypeptide or (b) as an insertion and/or replacement of amino acids at a position that is downstream of the final, carboxy-terminal β-sheet structure of the constant region of the light chain polypeptide. In some embodiments, a therapeutic polypeptide can be incorporated into a β-turn region of the light chain polypeptide constant region, which β-turn is structurally at a position that would allow the incorporated therapeutic peptide to be presented at the central cleft of the antibody.

One of ordinary skill in the art would know how to determine which amino acid or sequence of amino acids within the constant region of a light chain polypeptide would be amenable to such additions, insertions, or replacements. For example, any number of freely available computer programs can be used to model the three-dimensional structure of an antibody or fragment thereof, e.g., to identify an appropriate light chain constant region β-turn region into which a therapeutic peptide can be incorporated. Suitable computer programs include, e.g., C3nD and Rasmol, both of which are available electronically from the U.S. National Center for Biotechnology Information/National Institutes of Health and the U.S. National Science Foundation, respectively. Additional programs include, e.g., JMol, YASARA, Oscail, TINKER, MAGE, ArgusLab, and SwissPDB Viewer.

In one example, a skilled artisan can use C3nD to visualize the molecular structure of a human anti-tetanus toxoid Fab antibody fragment described in Faber et al. (1998) *Immunotechnology* 3(4):253-270. (See also MMDB Id No. 6997.) The artisan could identify within the fragment the light chain carboxy-terminal β-turn sequence: "EQWKSHK" (SEQ ID NO:13) as a potential suitable site for incorporation of a therapeutic peptide. The artisan could also identify within the fragment the light chain carboxy-terminal amino acid sequence: "PAECS" (SEQ ID NO:14) as a potential suitable site for incorporation of the therapeutic peptide. In other example, C3nD can be used to visualize the molecular structure of a human Fab fragment of the 2F5 antibody that binds to an epitope within HIV-1 gp140. (See MMDB Id No. 65747.) A skilled artisan could thus identify within the fragment the light chain carboxy-terminal β-turn sequences: "SDEQLKS" (SEQ ID NO:15) and "ADYEKH" (SEQ ID NO:16) and/or the light chain carboxy-terminal amino acid sequence: "GEC" as potentially structurally compatible with incorporation of a therapeutic peptide in accordance with the disclosure. The amino acid sequences of structurally similar regions of other antibodies can be identified using, e.g., Kabat et al. (1991) "Sequences of Proteins of Immunological Interest," Volume 1, $5^{th}$ Edition, U.S. Department of Health and Human Services, National Institutes of Health (NIH Publication No. 91-3242).

In such embodiments, the therapeutic peptide can be inserted into, and/or the incorporation of the peptide can replace all or part of, the subject constant region of a light chain polypeptide (e.g., a β-turn region of the constant region or a region that is downstream of the final β-sheet structure). As used herein, "part of the constant region of a light chain polypeptide" refers to at least 1 (e.g., at least 2, 3, 4, 5, 6, 7, 8, 9, 10, 11, or 12 or more) amino acids of the region. Thus, in some embodiments, at least 5 amino acids of the constant region of the light chain polypeptide can be replaced with a therapeutic peptide (e.g., a TPO mimetic peptide). It is understood that the replacement need not be one for one, i.e., one amino acid of the original light chain constant region is replaced with one amino acid of a therapeutic peptide (e.g., a TPO mimetic peptide). For example, the final five (5) amino acids of the light chain constant region can be deleted and replaced with a 14 amino acid TPO mimetic peptide (e.g., the TPO mimetic peptide having the amino acid sequence depicted in SEQ ID NO:1), thereby resulting in a partial replacement of the light chain carboxy-terminal region and effectively an addition of nine amino acids at the end of the light chain. In another example, five (5) amino acids of a β-turn region of a light chain polypeptide constant region can be replaced with a 14 amino acid TPO mimetic peptide (e.g., the TPO mimetic peptide having the amino acid sequence depicted in SEQ ID NO:1), thereby resulting in a partial replacement of the β-turn region and effectively an insertion of nine amino acids.

In embodiments where the therapeutic peptide (e.g., a TPO mimetic peptide) is incorporated into the hinge region itself, the therapeutic peptide can be an insertion and/or all or part of a hinge region can be replaced with the therapeutic peptide. As used herein, "part of a hinge region" refers to at least 1 (e.g., at least 2, 3, 4, 5, 6, 7, 8, 9, 10, 11, 12, 13, 14, 15, 16, 17, 18, 19, 20, 21, 22, 23, 24, or 25 or more) amino acids of a hinge region of an antibody. Thus, in some embodiments, at least 5 amino acids of a hinge region can be replaced with a therapeutic peptide (e.g., a TPO mimetic peptide). Part of the hinge region can include amino acids at the amino-terminus or carboxy-terminus of the hinge region of a heavy chain polypeptide, or the part can include amino acids internal to the hinge region. It is understood that the replacement need not be one for one, i.e., one amino acid of the original hinge region replaced with one amino acid of a therapeutic peptide (e.g., a TPO mimetic peptide). For example, five (5) amino acids of the amino-terminus of a hinge region can be deleted and replaced with a 14 amino acid TPO mimetic peptide (see, e.g., SEQ ID NO:1), thereby resulting in a partial replacement of the hinge and effectively an insertion of nine amino acids between the heavy chain constant region 1 (CH1) and the partial hinge. However, in some embodiments, e.g., 14 amino acids of the hinge region can be replaced with an equivalent 14 amino acids of a therapeutic peptide (such as a TPO mimetic peptide having the amino acid sequence depicted in SEQ ID NO:1 or 2). In some embodiments, the entire hinge region is replaced with a therapeutic peptide. In embodiments where part or all of the hinge region is replaced with a therapeutic peptide, it may be useful to include a spacer amino acid sequence flanking one or both of the amino-terminal and carboxy-terminal ends of the peptide (see below).

Accordingly, in some embodiments a therapeutic antibody (e.g., a TPO mimetic antibody) can contain two (2) light chain polypeptides, each containing at least one therapeutic peptide, and two heavy chain polypeptides that do not contain therapeutic peptides. In some embodiments, a therapeutic antibody described herein can contain two heavy chain polypeptides, each containing at least one therapeutic peptide (e.g., a TPO mimetic peptide) and two light chain polypeptides that do not contain therapeutic peptides. In yet another example, a therapeutic antibody (e.g., a TPO mimetic antibody) can contain two heavy chains and two light chains, wherein each of the heavy and light chain polypeptides contains at least one therapeutic peptide (e.g., a TPO mimetic peptide) in accordance with the disclosure.

In some embodiments, the therapeutic peptide in each of the light chain and heavy chain polypeptides can be the same therapeutic peptide. For example, each of the light chain and heavy chain polypeptides can have the same TPO mimetic peptide (e.g., the TPO mimetic peptide having the amino acid sequence depicted in SEQ ID NO:1). In some embodiments, the therapeutic peptide in the light chain polypeptides can be different from the therapeutic peptide in the heavy chain polypeptides. For example, an antibody can include two light chain polypeptides, each containing a first TPO mimetic peptide (e.g., having the amino acid sequence depicted in SEQ ID NO:1), and two heavy chain polypeptides, each containing a second TPO mimetic peptide (e.g., having the amino acid sequence depicted in SEQ ID NO:2).

In some embodiments, a therapeutic antibody can be dually-therapeutic in that one "arm" (e.g., an Fab region) of the therapeutic antibody contains one type of therapeutic peptide (e.g., a TPO mimetic peptide) and the second "arm" (e.g., the second Fab region) of the therapeutic antibody contains a different type of therapeutic peptide (e.g., an EPO mimetic peptide), both in accordance with the disclosure (see below).

It is understood that a therapeutic antibody can contain more than two (e.g., more than three, four, five, six, seven, eight, nine, 10, 11, 12, or 15 or more) therapeutic peptides so long as at least one of the therapeutic peptides is incorporated into a heavy chain or a light chain in accordance with the disclosure. In some embodiments where a therapeutic antibody contains more than two therapeutic peptides, at least one of the therapeutic peptides is incorporated into the light chain in accordance with the disclosure and at least one of the therapeutic peptides is incorporated into the heavy chain in accordance with the disclosure.

The location of, and amino acid sequences for, the hinge region within the heavy chain of an antibody are well known to those of skill in the art. Exemplary hinge region amino acid sequences are set forth in FIG. 28 of PCT Publication No. WO07/048,022, the disclosure of which (particularly FIG. 28) is incorporated herein by reference in its entirety.

In some embodiments, at least one (e.g., two, three, four, or all of the) therapeutic peptide(s) of the therapeutic antibody includes, or consists of, a TPO mimetic peptide having the amino acid sequence IEGPTLRQWLAARA (SEQ ID NO:1) or IEGPTLRQWLAARAP (SEQ ID NO:2). In some embodiments, at least one (e.g., two, three, four, or all of the) therapeutic peptide(s) of the therapeutic antibody includes, or consists of, a TPO mimetic peptide having the amino acid sequence depicted in FIG. 5 of U.S. Patent Application Publication No. 20030049683, the disclosure of which (particularly FIG. 5) is incorporated by reference in its entirety. In some embodiments, at least one (e.g., two, three, four, or all of the) therapeutic peptide(s) of the therapeutic antibody includes, or consists of, a TPO mimetic peptide having the amino acid sequence depicted in Table 1 or Table 2 of U.S. Pat. No. 6,083,913, the disclosure of which (particularly Table 1 and Table 2) is incorporated herein by reference in its entirety.

Additional therapeutic peptides that can be included in the therapeutic antibodies described herein include, e.g., other mimetic peptides such as, but not limited to, an EPO mimetic peptide. For example, suitable EPO mimetic peptides include, e.g., DYHCRMGPLTWVCKPLGG (SEQ ID NO: 3) or any of the EPO mimetics described in, e.g., U.S. Pat. Nos. 5,835,382 and 5,830,851. Other examples include peptides that bind to receptors which are activated by ligand-induced homo-dimerization including active fragments displaying G-CSF activity, GHR activity, and prolactin activity as described in Whitty and Borysenko (1999) *Chem. Biol.* 4:R107-18. Further examples of suitable peptides include a nerve growth factor mimetic from the CD loop as described in Zaccaro et al. (2000) *Med. Chem.* 43(19):3530-40; an IL-2 mimetic as described in Eckenberg et al. (2000) *J. Immunol.* 165(8):4312-8; glucagon-like peptide-1 as described in Evans et al. (1999) *Drugs R. D.* 2(2):75-94; FasL peptide that is capable of promoting apoptosis and is involved in, e.g., T-cell homeostasis, immune privilege, and maternal tolerance (see, e.g., Sheikh et al. (2000) *Leukemia* 14(8):1509-1513); the insulin c-peptide; the insulin β-chain; and tetrapeptide I (D-lysine-L-asparaginyl-L-prolyl-L-tyrosine) which stimulates mitogen activated B cell proliferation as described in Gagnon et al. (2000) *Vaccine* 18(18):1886-92. The therapeutic peptides (e.g., mimetic peptides) can have agonist or antagonist activity towards their cognate ligand or receptors. For example, peptides which exhibit receptor antagonistic activity for use in the therapeutic antibodies described herein can include, e.g., an amino-terminal peptide of vMIP-II as an antagonist of CXCR4 for use in treating HIV as described in Luo et al. (2000) *Biochemistry* 39(44):13545-50; an antagonist peptide ligand "AFLARAA" (SEQ ID NO:4) of the thrombin receptor for antithrombotic therapy as described in Pakala et al. (2000) *Thromb. Res.* 100(1):89-96; a peptide CGRP receptor antagonist CGRP (8-37) for attenuating tolerance to narcotics as described in Powell et al. (2000) *Br. J. Pharmacol.* 131(5):875-84; a parathyroid hormone (PTH)-1 receptor antagonist as described in Hoare et al. (2000) *Pharmacol. Exp. Ther.* 295(2):761-70; integrin-specific peptidomimetic antagonists for use in treating coronary thrombosis, asthma, inflammatory bowel disease, and/or cancer as described in, e.g., PCT Publication No. WO97/36858, Tcheng et al. (1995) *Circulation* 91:2151 and Bovy et al. (1994) *Bioorg. Med. Chem* 2:881; an opioid growth factor as described in Zagon et al. (2000) *Int. J. Oncol.* 17(5):1053-61; a high affinity type I interleukin I receptor antagonist as disclosed in Yanofsky et al. (1996) *Proc. Natl. Acad. Sci. USA* 93:7381-7386 and Vigers et al. (2000) *J. Biol. Chem.* 275 (47):36927-36933; an acid fibroblast growth factor binding peptide as described in Fan et al. (2000) *IUBMB Life* 49(6):545-48; and mimetic peptides useful for treating angiogenesis in a subject as described in, e.g., Mazitschek et al. (2002) *Mini Rev Med Chem* 2(5):491-506.

Methods for identifying additional therapeutic peptides (e.g., peptidomimetics) are known in the art. For example, to identify a region of a protein that is involved in a specific biological function, a survey of the shorter peptide fragments making up that protein may reveal the linear peptide epitope responsible. Alternatively, by surveying libraries of random peptides, a peptide that represents an optimal linear epitope or a discontinuous epitope can be discovered that mimics the activity of the natural protein. One method for selection is termed peptide phage-display. In this approach, a random peptide epitope library is generated so that peptides are present on the surface of a bacteriophage particle. These collections, or libraries, of peptides can then be surveyed for those able to bind to a specific immobilized target protein. See, e.g., Kieber-Emmons et al. (1997) *Curr Opin Biotechnol* 8(4):435-441; Gentilucci et al. (2006) *Curr Med Chem* 13(20):2449-2466; Pasqualini et al. (1995) *J. Cell Biol.* 130:1189-1196; Wrighton et al. (1996) *Science* 273:458-463; Cwirla et al. (1997) *Science* 276:1696-1699; Koivunen et al. (1993) *J. Biol. Chem.* 268:20205-20210; Koivunen et al. (1995) *Bio/Technol.* 13:265-270; Healy et al. (1995) *Biochem.* 34:3948-3955; Pasqualini et al. (1995) *J. Cell Biol.* 130:1189-1196. Alternative peptide selection systems are also possible including cell surface display and ribosomal display.

As used herein, "polypeptide," "peptide," and "protein" are used interchangeably and refer to any peptide-linked chain of amino acids, regardless of length or post-translational modification.

In some embodiments, a therapeutic peptide (e.g., a TPO mimetic peptide) can be flanked at one or both of the carboxy-terminus and the amino-terminus with a spacer amino acid sequence (or spacer sequence). The spacer sequence can be used, e.g., to reduce structural constraints on the mimetic, to allow the mimetic to more easily assume a biologically-active conformation, and/or to more efficiently present the peptide within the context of the antibody scaffold. In some embodiments, a spacer sequence can include, without limitation, one or more (e.g., two, three, four, five, six, seven, eight, nine, 10, 11, 12, 13, 14, 15, 20, 25, or 30 or more) amino acids. The spacer sequence can include, e.g., one or more proline or glycine residues. In some embodiments, the spacer amino acid sequence can be, or contain, amino acids ARSL (SEQ ID NO:5). In some embodiments, the spacer amino acid sequence can include, or be, "PI" (SEQ ID NO:6), "NP" (SEQ ID NO:7), or "LVG" (SEQ ID NO:8). In some embodiments, the TPO mimetic can have an "ARSL" spacer sequence (SEQ ID NO: 5) at the amino-terminus and a "LVG" spacer sequence (SEQ ID NO: 8) at the carboxy-terminus.

Any antibody (or fragment of an antibody) can serve as a scaffold sequence into which the therapeutic peptides (e.g., TPO mimetic peptides) are grafted. However, where the antibodies, or their fragments, are to be used in humans, the antibodies will preferably be human antibodies or humanized antibodies. One suitable antibody for use as a scaffold is the human anti-tetanus toxoid (TT) antibody or a fragment thereof (e.g., a Fab fragment). See, e.g., Barbas et al. (1994) *J. Am. Chem. Soc.* 116:2161-2162 and Barbas et al. (1995) *Proc. Natl. Acad. Sci. USA* 92:2529-2533. Other suitable antibodies for use as scaffolds in accordance with the disclosure include, e.g., anti-anthrax antibodies (e.g., anti-anthrax PA83 or anti-anthrax PA63 antigen antibodies) as set forth in the working Examples.

In some embodiments, one or more complementarity determining regions (CDRs) of the scaffold antibody can be modified (e.g., substituted, deleted, or post-translationally modified) in a manner sufficient to change, or partially or fully ablate, the antigen-binding specificity of the antibody. Methods for modifying a CDR of an antibody are well known in the art of molecular biology and described in, e.g., Sambrook et al. (1989) "Molecular Cloning: A Laboratory Manual, 2$^{nd}$ Edition," Cold Spring Harbor Laboratory Press, Cold Spring Harbor, N.Y. and Ausubel et al. (1992) "Current Protocols in Molecular Biology," Greene Publishing Associates. Furthermore, methods for determining whether an antibody binds to a protein antigen and/or the affinity (or loss of affinity) of an antibody for a protein antigen are known in the art. For example, the binding of an antibody to a protein antigen can be detected and/or quantified using a variety of techniques such as, but not limited to, Western blot, dot blot, plasmon surface resonance method (e.g., BIAcore system; Pharmacia Biosensor AB, Uppsala, Sweden and Piscataway, N.J.), or enzyme-linked immunosorbent assay (ELISA) assays. See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2$^{nd}$ Edition, Oxford University Press, NY, Oxford; Johne et al. (1993) *J. Immunol. Meth.* 160:191-198; Jonsson et al. (1993) *Ann. Biol. Clin.* 51:19-26; and Jonsson et al. (1991) *Biotechniques* 11:620-627. See also U.S. Pat. No. 6,355,245. Such techniques are also useful for determining whether a therapeutic peptide (e.g., a TPO mimetic peptide) within the context of a therapeutic antibody retains the ability to bind to its cognate target (e.g., a cell surface receptor such as c-Mpl). For example, suitable methods for determining the affinity of a TPO mimetic antibody for c-Mpl are set forth in the working Examples.

In some embodiments, one or more of the Fc constant regions (e.g., CH2, CH3, or CH4) of a therapeutic antibody (e.g., a TPO mimetic antibody) can be modified to partially or completely eliminate their ability to bind to Fc receptors expressed on host cells. Modifications include, e.g., mutagenesis of one or more of the Fc constant regions as well as post-translational modifications. In some embodiments, a therapeutic antibody (e.g., TPO mimetic antibody) can be modified such that the antibody has less than 50 (e.g., less than 45, 40, 35, 30, 25, 20, 15, 10, nine, eight, seven, six, five, four, three, two, one, 0.5, or less than 0.01) % of the ability of the unmodified therapeutic antibody to bind to an Fc receptor. Methods for determining whether an antibody binds to an Fc receptor are known in the art and described in, e.g., Lund et al. (1991) *J. Immunol.* 147(8):2657-62.

In some embodiments, at least part of a therapeutic antibody (e.g., a TPO mimetic antibody) can include an amino acid sequence encoded by the nucleotide sequence depicted in SEQ ID NO:9. In some embodiments, at least part of a therapeutic antibody (e.g., a TPO mimetic antibody) can include an amino acid sequence encoded by the nucleotide sequence depicted in SEQ ID NO:11. In some embodiments, a therapeutic antibody (e.g., a TPO mimetic antibody) can contain, or consist of, a light chain amino acid sequence encoded by the nucleotide sequence depicted in SEQ ID NO:9 and a heavy chain amino acid sequence encoded by the nucleotide sequence depicted in SEQ ID NO:11.

In some embodiments, at least part of a therapeutic antibody (e.g., a TPO mimetic antibody) can include a light chain polypeptide having the following amino acid sequence: <u>DIQMTQSPSSLSASV-GDRVTLTCRASQGVRNALVWYQQKPGKAPERLIYA-ASILQSGVPSRFSGSGSGTEFTLTIGGLQPEDFATYYC-LQHNSYPWTFGQGTKVEIKRT</u>VAAPSVFIFPPSDE-QLKSGTASWCLLNNFYPREAKVQWKVDNALQSGN-SQES VTEQDSKDSTYSLSSTLTLSKADYEKHKVY-ACEVTHQGLSSPVTKSFNRGECARSLI EGPTL-RQWLAARAPI (SEQ ID NO:10). In some embodiments, at least part of a therapeutic antibody (e.g., a TPO mimetic antibody) can include a heavy chain polypeptide having the following amino acid sequence: <u>QVQLVQSGAEVKKPGASVKVSCKASGYTFTYYA-MHWVRQAPGQRPEWMGWINGGDGKTKYAQKFQ-GRLAITRDTSARTAYMELISLTSEDTAVYYCAKGAE-MTVGSWGPGTLVTVSSA</u>STKGPSVFPLAPCSRSTSES-TAALGCLVKDYFPEPVTVS WNSGALTSGVHTFPAV-LQSSGLYSLSSVVTVPSSNFGTQTYTCNVDHKPSNT-KVDK TVERKCCVECPPCPAPPVANPIEGPTL-RQWLAARARGGPSVFLFPPKPKDTLM ISRTPEVTCVWDVSQEDPEVQFNWYVDGVEVHNAK-TKPREEQFNSTYRVVSVLTV LHQDWLNGKEYKCK-VSNKGLPSSIEKTISKAKGQPREPQVYTLPPSQEEMT-KNQV SLTCLVKGFYPSDIAVEWESNGQPENNYKTTPPV-LDSDGSFFLYSRLTVDKSRWQE GNVFSCSVM-HEALHNHYTQKSLSLSLGK (SEQ ID NO:12). (Above: antibody variable region sequences are underlined; the TPO mimetic peptide amino acid sequence in each polypeptide is in bold; and antibody constant region amino acid sequences are italicized. Non-emphasized amino acid sequences correspond to spacer sequences.)

As used throughout the present disclosure, the terms "therapeutic antibody" and "TPO mimetic antibody" refer to a whole or intact antibody (e.g., IgM, IgG (including IgG1, IgG2, IgG3, and IgG4), IgA, IgD, or IgE) molecule that contains at least two (e.g., at least two, three, or four) therapeutic peptides (e.g., TPO mimetic peptides) in accordance with the disclosure. The therapeutic antibodies (e.g., TPO mimetic antibodies) also include whole antibodies having at least two therapeutic peptides and a hybrid constant region, or a portion thereof, such as a G2/G4 hybrid constant region (see e.g., Burton et al. (1992) *Adv. Immun.* 51:1-18; Canfield et al. (1991) *J. Exp. Med.* 173:1483-1491; and Mueller et al. (1997) *Mol. Immunol.* 34(6):441-452). For example (and in accordance with Kabat numbering), the IgG1 and IgG4 constant regions contain $G_{249}G_{250}$ residues whereas the IgG2 constant region does not contain residue 249, but does contain $G_{250}$. In a G2/G4 hybrid constant region, where the 249-250 region comes from the G2 sequence, the constant region can be further modified to introduce a glycine residue at position 249 to produce a G2/G4 fusion having $G_{249}/G_{250}$. Other constant domain hybrids that contain $G_{249}/G_{250}$ can also be used as scaffolds for TPO mimetic antibodies in accordance with the disclosure.

The term "antibody" includes, e.g., a chimerized or chimeric antibody, a humanized antibody, a deimmunized human antibody, and a fully human antibody. The antibody scaffold can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice.

As used herein, the term "therapeutically-active antibody fragment," or in some cases "antibody fragment" or "therapeutically-active fragment," refers to a fragment of a therapeutic antibody (e.g., a fragment of a TPO mimetic antibody) that: (i) structurally retains at least two (e.g., at least two, three, or four; see supra) of the therapeutic peptides (e.g., TPO mimetic peptides) present in the intact therapeutic antibody in accordance with the disclosure; and (ii) functionally retains at least 10% (e.g., at least 12%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, at least 99.5%, or 100% or more) of the therapeutic activity of the intact therapeutic antibody. For example, a therapeutically-active fragment of a TPO mimetic antibody described herein would retain at least 10% of the TPO-like activity of the intact TPO mimetic antibody (see below under "Methods for Producing a Therapeutic Antibody or Therapeutically-Active Fragment Thereof"). In another example, a therapeutically-active fragment of an antibody containing an erythropoietin (EPO) mimetic peptide would retain at least 10% of the EPO-like activity of the intact "EPO mimetic antibody." Therapeutically-active fragments of a therapeutic antibody include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, minibodies, triabodies, and diabodies (see, e.g., Todorovska et al. (2001) *J Immunol Methods* 248(1):47-66; Hudson and Kortt (1999) *J Immunol Methods* 231(1):177-189; and Poljak (1994) *Structure* 2(12): 1121-1123, the disclosures of each of which are incorporated herein by reference in their entirety) fused to at least a portion of a heavy chain and/or light chain constant region and containing at least two therapeutic peptides in accordance with the disclosure can be prepared and used in the methods described herein.

In some embodiments, bispecific antibodies (or a fragment thereof such as a F(ab')$_2$) can serve as a scaffold for the introduction of the at least two therapeutic peptides in accordance with the disclosure. In some embodiments, the antigen-binding ability of at least one (or both) of the antigen combining sites of the bispecific antibody is (are) maintained. For example, two or more therapeutic peptides can be incorporated into one arm (e.g., an Fab region) of a bispecific antibody in accordance with the disclosure, but not incorporated into the second arm (e.g., the second Fab region) of a bispecific antibody. In another example, therapeutic peptides can be incorporated into both arms (e.g., both of the Fab regions) of a bispecific antibody, wherein the antigen-binding ability of at least one (or both) of the antibody arms is (are) unaffected by incorporation of the therapeutic peptides. Such a therapeutic bispecific antibody (which is fully embraced by the term "therapeutic antibody") can be used, e.g., to target the therapeutic peptides of the therapeutic antibody to a particular target cell. For example, where a therapeutic bispecific antibody contains TPO mimetic peptides, at least one antigen combining site of the therapeutic bispecific antibody can bind to a protein marker on a megakaryocyte. Suitable megakaryocyte protein markers include, e.g., CD41 (IIb/IIIa) and CD42 (Ib).

Methods for Producing a Therapeutic Antibody or Therapeutically-Active Fragment Thereof The therapeutic antibodies (e.g., the TPO mimetic antibodies) or therapeutically-active fragments thereof can be produced using a variety of techniques known in the art of molecular biology and protein chemistry. For example, grafting of a DNA sequence encoding a therapeutic peptide (e.g., a TPO mimetic peptide) into a DNA sequence encoding an antibody, so as to replace the hinge region of the antibody with the peptide sequence, can be carried out using recombinant DNA techniques such as, but not limited to, PCR overlap, restriction enzyme site cloning, site specific mutagenesis and completely synthetic means. Site-specific mutagenesis can be accomplished in several ways. One is based on dut/ung Kunkel mutagenesis (Kunkel (1985) *Proc. Natl. Acad. Sci. USA* 82:488-92). Several PCR amplification-based mutagenesis approaches are also commercially available such as the QuickChange® Site-Directed Mutagenesis Kit and the ExSite™ PCR-based Site-Directed Mutagenesis Kit (Stratagene, La Jolla, Calif.). Another non-PCR method is the GeneEditor™ in vitro Site-Directed Mutagenesis System (Promega Corporation, Madison, Wis.). Completely synthetic means are also well-known and described, e.g., in Deng et al. (1995) *Methods Mol. Biol.* 51:329-42; Kutemeier et al. (1994) *Biotechniques* 17(2): 242-246; Shi et al. (1993) *PCR Methods Appl.* 3(1):46-53; and Knuppik et al. (2000) *J. Mol. Biol.* 296(1):571-86.

Standard molecular biology techniques can also be used to introduce flanking, spacer amino acid sequences to the carboxyl and/or amino terminal ends of the therapeutic peptide (e.g., the TPO mimetic peptide). As described above, such flanking sequences can be useful, e.g., to reduce structural constraints on the therapeutic peptide and to allow the peptide to more easily adopt a conformation necessary for biological activity.

In some embodiments, a flanking region can include, e.g., one or more proline residues. See, e.g., Kini and Evans (1995) *Biochem Biophys Res Commun* 212(3):115-24 and Kini et al. (1995) *FEBS Letters* 375:15-17. In some embodiments, one or more proline residues are added to the carboxy terminus of the therapeutic peptide (e.g., the TPO mimetic peptide).

In some embodiments, the spacer amino acid sequences can include e.g., one or more of any of SEQ ID NOs:5-8.

The nucleic acids can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc. Natl. Acad. Sci. USA,* 78:2072) or Tn5 neo (Southern and Berg (1982) *Mol. Appl. Genet.* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc. Natl. Acad. Sci. USA,* 79:7147), polyoma virus (Deans et al. (1984) *Proc. Natl. Acad. Sci. USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, lipofectin, electroporation, viral infection, dextran-mediated transfection, polybrene-mediated transfection, protoplast fusion, and direct microinjection.

Appropriate host cells for the expression of therapeutic antibodies (e.g., TPO mimetic antibodies), or therapeutically-active fragments thereof, include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, a therapeutic antibody can be expressed in, and purified from, transgenic animals (e.g., transgenic mammals). For example, therapeutic antibodies can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The therapeutic antibodies (e.g., TPO mimetic antibodies) and fragments thereof are produced from cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, therapeutic antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. Therapeutic antibodies (e.g., TPO mimetic antibodies), or fragments thereof, can be expressed in mammalian cells or in other expression systems including but not limited to yeast, baculovirus, and in vitro expression systems (see, e.g., Kaszubska et. al. (2000) *Protein Expression and Purification* 18:213-220).

Following expression, the therapeutic antibodies (e.g., TPO mimetic antibodies) or fragments thereof can be isolated. The term "purified" or "isolated" as applied to any of the proteins described herein (e.g., the TPO mimetic antibody proteins or fragments thereof) refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

The therapeutic antibodies (e.g., TPO mimetic antibodies) or their fragments can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, a TPO mimetic antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, $3^{rd}$ edition," Springer-Verlag, New York City, N.Y. The degree of purification necessary will vary depending on the desired use. In some instances, no purification of the expressed therapeutic antibodies (e.g., the TPO mimetic antibodies), or fragments, will be necessary.

Methods for determining the yield or purity of a purified therapeutic antibody (e.g., a TPO mimetic antibody) or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, endotoxin can be removed from the therapeutic antibodies or fragments. Methods for removing endotoxin from a protein sample are known in the art and exemplified in the working examples. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Mirus), or Acrodisc™-Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000

Chromogenic kit (BioWhittaker), the limulus amebocyte lysate (LAL)-based kits such as the Pyrotell®, Pyrotell®-T, Pyrochrome®, Chromo-LAL, and CSE kits available from the Associates of Cape Cod Incorporated.

Suitable methods for generating and purifying a therapeutic antibody are also set forth in the working Examples.

Modification of the Therapeutic Antibodies and Fragments

The therapeutic antibodies (e.g., TPO mimetic antibodies), or therapeutically-active fragments thereof, can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the therapeutic antibody or fragment proteins.

In some embodiments, the therapeutic antibodies, or therapeutically-active fragments thereof, can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, or a luminescent label. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the therapeutic antibodies or fragments. Heterologous polypeptides also include polypeptides that are useful as diagnostic or detectable markers, for example, luciferase, green fluorescent protein (GFP), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), GFP, DyLight 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA). Enzymatic labels include, e.g., alkaline phosphatase, CAT, luciferase, and horseradish peroxidase.

Two proteins (e.g., a TPO mimetic antibody and a heterologous amino acid sequence) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4[p-azidosalicylamido]butylamine), and an amino group and a guanidinium group that is present in the side chain of arginine (e.g., p-azidophenyl glyoxal monohydrate).

A radioactive label can be directly conjugated to the amino acid backbone of the protein. Alternatively, the radioactive label can be included as part of a larger molecule (e.g., $^{125}I$ in meta-[$^{125}I$]iodophenyl-N-hydroxysuccinimide ([$^{125}I$] mIPNHS) which binds to free amino groups to form meta-iodophenyl (mIP) derivatives of relevant proteins (see, e.g., Rogers et al. (1997) *J. Nucl. Med.* 38:1221-1229) or chelate (e.g., to DOTA or DTPA) which is in turn bound to the protein backbone. Methods of conjugating the radioactive labels or larger molecules/chelates containing them to therapeutic antibodies, or therapeutically-active fragments thereof, are known in the art. Such methods involve incubating the proteins with the radioactive label under conditions (e.g., pH, salt concentration, and/or temperature) that facilitate binding of the radioactive label or chelate to the protein (see, e.g. U.S. Pat. No. 6,001,329).

Methods for conjugating a fluorescent label (sometimes referred to as a "fluorophore") to a protein (e.g., a therapeutic antibody or therapeutically-active fragment thereof) are known in the art of protein chemistry. For example, fluorophores can be conjugated to free amino groups (e.g., of lysines) or sulfhydryl groups (e.g., cysteines) of proteins using succinimidyl (NHS) ester or TFP ester moieties attached to the fluorophores. In some embodiments, the fluorophores can be conjugated to a heterobifunctional cross-linker moiety such as sulfo-SMCC. Suitable conjugation methods involve incubating the therapeutic antibody proteins, or fragments thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

As described above, the therapeutic antibodies, or therapeutically-active fragments thereof, described herein provide an increased serum half-life to the therapeutic peptides contained therein. However, in some embodiments, the antibodies or fragments can be modified, e.g., with a moiety that improves the stabilization and/or retention of the antibodies themselves in circulation, e.g., in blood, serum, or other tissues. For example, the antibody or fragment can be PEGylated as described in, e.g., Lee et al. (1999) *Bioconjug. Chem.* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody (or fragment) by at least 1.5 (e.g., at least 2, 5, 10, 15, 20, 25, 30, 40, or 50 or more) fold. The stabilization moiety can further improve the stability, or retention of, the therapeutic peptide (as compared to the free form therapeutic peptide) by at least 1.5 (e.g., at least 2, 5, 10, 15, 20, 25, 30, 40, or 50 or more) fold.

Assaying the Biological Activity of the Therapeutic Antibodies or Fragments

A variety of in vitro and in vivo biological assays can be used to assay the biological activity of a therapeutic antibody, or a therapeutically-active fragment of the antibody, described herein. The methods can vary depending on the activity of the particular therapeutic peptide contained in the antibodies. For example, thrombopoietin-like activity of TPO mimetic antibodies, fragments, or conjugates described can be assayed using, e.g., colony formation assays, proliferation assays, phosphorylation assays, and/or transcription-based assays. Colony formation assays measure megakaryocytic colonies formed from bone marrow samples obtained from a subject (see, e.g., Megacult® C Kit from Stem Cell Technologies Inc., Vancouver BC, Canada). Proliferation assays can be used to measure proliferation of c-Mpl receptor-expressing Ba/F3 cells in the presence, as compared to the absence, of the TPO mimetic antibodies, fragments, or conjugates. See, e.g., Cwirla et al. (1997) *Science* 276:1696-1699 and de Sauvage et al. (1994) *Nature* 369:533. An increase in proliferation of the cells contacted with the TPO mimetic antibodies (or fragments) as compared to the amount of proliferation of the cells in the absence of the TPO mimetic antibodies (or fragments) is an indication that the TPO mimetic antibodies (or fragments) have TPO-like biological activity. Activation of c-Mpl receptor, as a measure of the activity of a TPO mimetic antibody, can be assayed by measuring phosphorylation of JAK2 or Stat3 or Stat5 as described in, e.g., Drachman et al. (1999) *J. Biol. Chem.* 274:13480-13484 and Miyakawa et al. (1996) *Blood* 87(2): 439-46. The activity of a TPO mimetic antibody, or therapeutically-active fragment thereof, can be measured using a transcription-based assay as described in U.S. patent application publication no. 20030049683. For example, a mammalian cell can be transfected with a nucleic acid encoding a full length c-Mpl receptor and luciferase gene, whose expression is under the control of the c-Fos promoter. After allowing the cells to express the c-Mpl receptor, cells are contacted with the TPO mimetic antibody, or therapeutically-active fragment thereof, for a time and under conditions that allow for binding of the antibody to the receptor. An increase in the amount of luciferase produced in the cells, as compared to the amount of luciferase produced in cells that were not contacted with the antibody, is an indication that the TPO mimetic antibody has TPO-like activity.

In addition, the TPO-like activity of a TPO mimetic antibody, or therapeutically-active fragment thereof, can be assayed using a variety of in vivo techniques known in the art. For example, the production of platelet levels can be measured in a mouse following administration of a TPO mimetic antibody or fragment thereof. An increase in platelet production by the treated mouse, as compared to a mouse that did not receive treatment, is an indication that the TPO mimetic antibody, or fragment, has TPO-like activity. Exemplary in vivo assays (e.g., measuring platelet production in an animal and/or studying the effects of a TPO mimetic antibody survival of an animal exposed to radiation) are exemplified in the working examples.

For therapeutic antibodies (or fragments) containing erythropoietin (EPO) mimetic peptides, the EPO-like activity of the antibodies or fragments can be assayed using a bone marrow erythroid colony formation assay (see, e.g., Wrighton et al. (1996) *Science* 273:458-463); a human erythroleukemia cell proliferation assay (Kitamura et al. (1989) *J. Cell Physiol.* 140:323-334); and/or phosphorylation or transcriptional activation assays as described in, e.g., Witthuhn et al. (1993) *Cell* 74:227-236. For example, one useful in vitro assay utilizes an EPO-dependent UT-7/EPO cell line, derived from a patient with acute megakaryoblastic leukemia (see, e.g., Komatsu et al. (1993) *Blood* 82(2):456-464). UT-7/EPO cells undergo apoptosis after withdrawal of media supplemented with rHuEPO. However, the cells can be rescued if treated with rHuEPO or an EPO agonist. Thus, a therapeutic antibody containing EPO, or a therapeutically-active fragment thereof, can be contacted to starved UT-7/EPO cells and the viability of the cells can be determined. An increase in the survival of starved cells contacted with the therapeutic antibody, as compared to the survival of cells in the absence of the therapeutic antibody, is an indication that the therapeutic antibody has EPO-like activity.

Pharmaceutical Compositions

Compositions containing a therapeutic antibody (e.g., a TPO-mimetic antibody), or a therapeutically-active fragment thereof, described herein can be formulated as a pharmaceutical composition, e.g., for administration to a subject to increase platelet production. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J. Pharm. Sci.* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing an antibody or fragment intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating an antibody (or a fragment of the antibody) described herein in the required amount in an appropriate solvent with one or a combination of ingredients enumerated above, as required, followed by filtered sterilization. Generally, dispersions are prepared by incorporating an antibody or fragment described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of the therapeutic antibody (e.g., the TPO mimetic antibody), or a therapeutically-active fragment thereof, described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

In certain embodiments, the therapeutic antibody (e.g., the TPO mimetic antibody), or a therapeutically-active fragment thereof, can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

Nucleic acids encoding the therapeutic antibodies (e.g., the TPO mimetic antibodies), or therapeutically-active fragments thereof, can be incorporated into a gene construct to be used as a part of a gene therapy protocol to deliver nucleic acids that can be used to express and produce agents within cells (see below). Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized (e.g., antibody conjugated), polylysine conjugates, gramicidin S, artificial viral envelopes or other such intracellular carriers, as well as direct injection of the gene construct or $CaPO_4$ precipitation (see, e.g., WO04/060407) carried out in vivo. (See also, "Ex vivo Approaches," below.) Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am. J. Respir. Cell. Mol. Biol.* 7:349-356; Samulski et al. (1989) *J. Virol.* 63:3822-3828; and McLaughlin et al. (1989) *J. Virol* 62:1963-1973.

In some embodiments, a TPO mimetic antibody, or a therapeutically-active fragment thereof, can be formulated with one or more additional active agents useful for increasing platelet production in a subject. Additional agents for increasing platelet production in a subject include, without limitation, Promacta®/Revolade® (eltrombopag; GlaxoSmithKline), Nplate™ (romiplostim; Amgen, Inc.) and Neumega® (oprelvekin; rhIL-11, Genetics Institute, Inc.). In some embodiments, a TPO mimetic antibody, or a therapeutically-active fragment thereof, can be formulated with one or more additional active agents useful for treating anemia or neutropenia including, e.g., an erythropoiesis stimulating agent (ESA) or Neulasta™ (pegfilgrastim; Amgen, Inc.). ESAs include, without limitation, Procrit® (epoetin alfa; Ortho Biotech), Epogen® (epoetin alfa; Amgen, Inc.), and Aranesp® (darbepoetin alfa; Amgen, Inc.).

In some embodiments, a TPO mimetic antibody, or a therapeutically-active fragment thereof, can be formulated with one or more additional agents useful for treating a symptom of radiation exposure. For example, a TPO mimetic antibody or fragment can be formulated with an antibiotic, an anesthetic, an antiemetic, a steroid (e.g., an androstenediol such as 4-androstenediol or 5-androstenediol), a chelating agent, and a stem cell. Suitable antiemetics include, without limitation, a $5-HT_3$ receptor antagonist, a dopamine antagonist, and cannabinoids. See, e.g., Donnerer J. (2003) "Antiemetic Therapy," Karger Publishers (ISBN 3805575475). Formulation with chelating agents can be useful in embodiments where a subject to be treated is one exposed to a radionuclide such as cesium-137 or thallium-201. Suitable chelating agents include, e.g., Ca-DTPA, Zn-DTPA, Radiogardase™ (also referred to as "Prussian blue"), deferoximine, and penicillamine. In some embodiments, the TPO mimetic antibody or fragment thereof can be formulated with a radionuclide-displacing agent such as, but not limited to, potassium iodide or a calcium salt. In some embodiments, the TPO mimetic antibody or fragment thereof can be formulated with an agent for stimulating secretion of a radioisotope from a subject. For example, the antibody or fragment can be formulated with a diuretic.

In some embodiments, e.g., where a decreased platelet count in a subject results from an infection (e.g., infection-associated thrombotic thrombocytopenic purpura or DIC), the antibody or fragment thereof can be formulated with one or more agents for use in treating an infection (e.g., a bacterial infection or an infection with a virus such as HIV). For example, an antibody or fragment can be formulated with an antibiotic or an anti-viral agent. The antibiotic will vary depending on the type of infection, but can include, e.g., penicillin, erythromycin, clarithromycin, or doxycycline. Similarly, anti-viral agents will vary depending on the type of infection. For example, anti-viral agents useful for treating an HIV infection include, e.g., HIV protease inhibitors, HIV integrase inhibitors, HIV reverse transcriptase inhibitors, or agents that inhibit the binding and/or entry of HIV into a cell.

When a therapeutic antibody (e.g., a TPO mimetic antibody), or a therapeutically-active fragment thereof, is to be used in combination with a second active agent, the agents can be formulated separately or together. For example, the respective pharmaceutical compositions can be mixed, e.g., just prior to administration, and administered together, or each composition can be administered separately, e.g., at the same or different times (see below).

As described above, a composition can be formulated such that it includes a therapeutically effective amount (e.g., a platelet production-increasing amount) of a therapeutic antibody or a therapeutically-active fragment thereof, or the composition can be formulated to include a sub-therapeutic amount of the antibody and a sub-therapeutic amount of one or more additional active agents such that the components in total are therapeutically effective (e.g., therapeutically effective for treating a subject for radiation exposure or increasing platelet production in a subject). For example, a composition can include a subtherapeutic amount of each of TPO mimetic antibody and eltrombopag, such that the amount of both agents in total is therapeutically effective for a subject. Methods for determining a therapeutically effective dose are known in the art and described herein.

Methods for Treatment

Depending on the particular therapeutic peptide, the above-described compositions are useful in, inter alfa, a variety of methods for treatment. For example, the TPO mimetic antibodies are useful in methods for increasing platelet production in a subject (e.g., a human) in need thereof. The compositions can be administered to a subject, e.g., a human subject, using a variety of methods that depend, in part, on the route of administration. The route can be, e.g., intravenous injection or infusion (IV), subcutaneous injection (SC), intraperitoneal (IP), or intramuscular injection.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. (See, e.g., U.S. Patent Publication No. 20080241223; U.S. Pat. Nos. 5,501,856; 4,863,457; and 3,710,795; EP 488401; and EP 430539, the disclosures of each of which are incorporated herein by reference in their entirety.) The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

A suitable dose of a therapeutic antibody (e.g., a TPO mimetic antibody) or a therapeutically-active fragment thereof (e.g., a dose that is capable of increasing platelet production in a subject) can depend on a variety of factors including, e.g., the age, sex, and weight of a subject to be treated and the particular therapeutic antibody used. For example, a different dose of a TPO mimetic antibody may be required to increase platelet production in a subject as compared to the dose of a fragment of a TPO mimetic antibody required to treat the same subject. Other factors affecting the dose of a TPO mimetic antibody administered to the subject include, e.g., the cause of reduced platelet levels in the subject or the severity of the reduction in platelet count. For example, a subject having idiopathic thrombocytopenic purpura (ITP) may require administration of a different dosage of the TPO mimetic antibody (or fragment) than a subject suffering from radiation-induced thrombocytopenia. Other factors that affect the dosage of a particular therapeutic antibody (or fragment) can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

The therapeutic antibody (e.g., a TPO mimetic antibody) or fragment can be administered as a fixed dose, or in a microgram per kilogram (µg/kg) or milligram per kilogram (mg/kg) dose. In some embodiments, the dose can also be chosen to further reduce or avoid production of antibodies or other host immune responses against one or more active agents in the composition. While in no way intended to be limiting, exemplary dosages of an antibody or fragment thereof described herein include, e.g., 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, and 1-10 mg/kg. Exemplary dosages of a therapeutic antibody (e.g., a TPO mimetic antibody) include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, and 8 mg/kg.

A pharmaceutical composition can include a therapeutically effective amount of a therapeutic antibody (e.g., a TPO mimetic antibody) or therapeutically-active fragment thereof. Such effective amounts can be readily determined by one of ordinary skill in the art based, in part, on the effect of the administered antibody (or fragment), or the combinatorial effect of the antibody and one or more additional active agents, if more than one agent is used. A therapeutically effective amount of a therapeutic antibody (e.g., a TPO mimetic antibody), or fragment thereof, can also vary according to factors such as the disease state, age, sex, and weight of the individual, and the ability of the antibody (and one or more additional active agents) to elicit a desired response in the individual, e.g., an increase in platelet production in the subject. For example, a therapeutically effective amount of a TPO mimetic antibody, or fragment thereof, can increase platelet production in an individual and thus can, e.g., inhibit (lessen the severity of or eliminate the occurrence of) and/or prevent platelet depletion following radiation exposure or chemotherapy. A therapeutically effective amount of a therapeutic antibody is also one in which any toxic or detrimental effects of the composition are outweighed by the therapeutically beneficial effects.

The terms "therapeutically effective amount" or "therapeutically effective dose," or similar terms used herein are intended to mean an amount of an agent (e.g., a therapeutic antibody or fragment described herein) that will elicit the desired biological or medical response (e.g., an increase in platelet production in a subject). In some embodiments, a composition described herein contains a therapeutically effective amount of a therapeutic antibody (e.g., a TPO mimetic antibody) or a fragment thereof. In some embodiments, the composition contains a therapeutic antibody (e.g., a TPO mimetic antibody), or fragment thereof, and one or more (e.g., three, four, five, six, seven, eight, nine, 10, or 11 or more) additional therapeutic agents such that the composition as a whole is therapeutically effective. For example, a composition can contain a TPO mimetic antibody and eltrombopag, wherein the antibody and small molecule are each at a concentration that when combined are therapeutically effective.

Toxicity and therapeutic efficacy of such compositions can be determined by known pharmaceutical procedures in cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions of the therapeutic antibodies (e.g., TPO mimetic antibodies), or their therapeutically-active fragments, which exhibit high therapeutic indices are preferred. While compositions that exhibit toxic side effects may be used, care should be taken to design a delivery system that targets such compounds to the site of affected tissue and to minimize potential damage to normal cells and, thereby, reduce side effects.

Animal models suitable for assaying the toxicity and/or therapeutic efficacy of the therapeutic antibodies, or therapeutically-active fragments, described herein are known in the art. Such models will vary, of course, based in part on the biological activity of the particular therapeutic peptide contained in an antibody or fragment. For example, suitable animal models (e.g., mouse and non-human primate models) for assaying the therapeutic efficacy of a TPO mimetic antibody, or therapeutically-active fragment thereof, are known in the art as described in, e.g., Thomas et al. (1996) *Stem Cells* 14:244; Winton et al. (1995) *Experimental Hematology* 23:486; Neelis et al. (1998) *Blood* 92(5):1586-1597; and Mouthon et al. (1999) *Int J Radiat Oncol Biol Phys* 43(4):867-875. In addition, animal models suitable for assaying the toxicity and/or therapeutic efficacy of TPO mimetic antibodies are exemplified in the working examples.

The data obtained from the cell culture assays and animal studies can be used in formulating a range of dosage for use in humans. Suitable animal models for use in evaluating the compositions (e.g., TPO mimetic antibodies or fragments contained therein) are known in the art and exemplified in the working examples. The dosage of such therapeutic antibodies (e.g., TPO mimetic antibodies) or fragments lies generally within a range of circulating concentrations of the antibodies that include the $ED_{50}$ with little or no toxicity. The dosage may vary within this range depending upon the dosage form employed and the route of administration utilized. For a therapeutic antibody (e.g., a TPO mimetic antibody), or a therapeutically-active fragment thereof, used as described herein (e.g., for increasing platelet production in a subject), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Suitable human doses of therapeutic antibodies can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, art 1:523-531; and Hetherington et al. (2006) *Antimicrobial Agents and Chemotherapy* 50(10): 3499-3500.

As described above, the required dose of a TPO mimetic antibody or a therapeutically-active fragment thereof can be determined, in part, based on the platelet count in the subject's blood. For example, a subject having a lower platelet count may require a higher dose of a TPO mimetic antibody than a subject having higher platelet counts.

Any of the methods described herein that involve the use of TPO mimetic antibodies, or therapeutically-active fragments thereof, can include monitoring the platelet count following administration of the composition containing a TPO mimetic antibody or fragment thereof. Where the composition is to be administered in conjunction with a chemotherapy or radiotherapy regimen, the monitoring can occur before, during, and/or after exposure to the chemotherapy or radiotherapy regimen.

Methods for determining platelet counts in a blood-derived sample from a subject are well known in the art of medicine and described in, e.g., Sallah et al. (1998) *Postgraduate Medicine* 103:209-210; Kottke-Marchant (1994) *Hematol Oncol Clin North Am.* 8:809-853; Redei et al. (1995) *J Crit. Illn* 10:133-137; Butkiewicz et al. (2006) *Thrombosis Research* 118(2):199-204; Tomita et al. (2000) *Am J Hematol* 63(3):131-135; and Schrezenmeier et al. (1998) *Br J Haematol* 100(3):571-576.

It is understood that a medical practitioner may elect to alter the amount of the dose, the frequency of the dose, or the route of administration, of the composition based on the real-time monitoring of the subject's platelet levels.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a therapeutic antibody such as a TPO mimetic antibody). For example, a subject who has a disorder related to insufficient platelet levels (a thrombocytopenia-associated disease) can be a subject in need of treatment with a TPO mimetic antibody, or fragment thereof, described herein.

Accordingly, a TPO mimetic antibody, or a therapeutically-active fragment thereof, can be administered to a subject having a disorder related to insufficient platelet counts (thrombocytopenia). Such disorders are well known in the art of medicine and include, without limitation, Bernard-Soulier syndrome, idiopathic thrombocytopenic purpura (ITP), Wiskott-Aldrich syndrome, hypersplenism, thrombotic microangiopathies, disseminated intravascular coagulation (DIC), aplastic anemia, hemolytic uremic syndrome (HUS; typical or atypical), catastrophic antiphospholipid syndrome (CAPS), neonatal alloimmune ITP, post-transfusion purpura, paroxysmal nocturnal hemoglobinuria, uremia, von Willebrand disease, variant von Willebrand disease, Glanzmann's thrombasthenia, TTP, lupus, and vitamin deficiency. The disorders also include radiation-induced thrombocytopenia (see below) and drug-induced thrombocytopenia (DIT; also referred to as "drug-induced platelet insufficiency") such as, but not limited to, thrombocytopenia induced by heparin, cinchona alkaloid derivatives (quinine and quinidine), penicillin, sulfonamides, non-steroidal anti-inflammatory drugs (NSAIDs), anti-convulsants, antirheumatic and oral anti-diabetic drugs, gold salts, diuretics, rifampicin, interferon gamma, ribovarin, and ranitidine. See, e.g., Chong et al. (1991) *Blood* 77:2190-2199; Curtis et al. (1994) *Blood* 84:176-183; Gentilini et al. (1998) *Blood* 92:2359-2365; Burgess et al. (2000) *Blood* 95:1988-1992; van de Bemt et al. (2004) *Drug Saf.* 27:1243-1252; Aster and Bougie (2007) *New Eng J Med* 357(6):580-587; George et al. (1998) *Ann Intern Med* 129(11):886-890; and Li et al. (2007) *Drug Saf.* 30(2):185-186, the disclosure of each of which is incorporated herein by reference in its entirety. DIT can result from treatment of a variety of conditions such as, but not limited to, a neoplasm, myelodysplastic syndrome, and certain viral infections such as HIV and hepatitis infections. For example, DIT associated with chemotherapy regimens are further elaborated on below.

A TPO mimetic antibody, or fragment thereof, can also be administered to a patient in conjunction with a chemotherapeutic or radiotherapeutic regimen. Due to the myelosuppressive effects of chemotherapy or radiotherapy, patients who undergo these treatments can develop severe neutropenia and thrombocytopenia that is potentially life-threatening from the risk of hemorrhage. Thrombocytopenia can often limit the ability of medical practitioners (e.g., oncologists), e.g., to escalate chemotherapy dosages and/or sustain chemotherapy regimens, which in turn prevents or lessens the likelihood of remission of the cancer, or the cure of cancer patients. See, e.g., Neelis et al. (1997) *Blood* 90(7): 2565-2573; Allen et al. (2004) "Ansel's Pharmaceutical Dosage Forms and Drug Delivery Systems," Lippincott Williams & Wilkins (ISBN 0781746124); Beutler (1993) *Blood* 81:1411; and Niremburg (2003) *Cancer Nurs* 26(6): 325-375. Thus, TPO mimetic antibodies, or therapeutically-active fragments thereof, can be used by medical practitioners to accelerate platelet recovery in conjunction with a radiotherapy regimen or chemotherapy regimen (see below). As described above and exemplified in the working examples, the TPO mimetic antibodies described herein are highly effective in increasing total platelet levels in an animal. The TPO mimetic antibodies are also effective in quickly recovering depleted platelet levels in an animal. Thus, the TPO mimetic antibodies or fragments described herein, when administered to a subject with cancer, can allow a medical practitioner to administer a more potent dose or a more frequent dosing of a chemotherapy or a radiotherapy to the subject than would be safe in the absence of the TPO mimetic antibody (or fragment). As used in the above context, "safe" or "safely possible" refers to a determination by a medical practitioner of a platelet level in a subject that is sufficient to begin a therapeutically effective chemotherapy or radiotherapy regimen in the subject.

Accordingly, the TPO mimetic antibody or fragment can be administered to a subject prior to, during, and/or after administration of the chemotherapy regimen or radiotherapy regimen. As described above, subjects in need of a chemotherapy or radiotherapy regimen include those subjects having a cancer. For example, a subject can have a cancer selected from the group consisting of lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, and bladder cancer.

Subjects in need of a chemotherapy or radiotherapy regimen also include those subjects having an inflammatory or autoimmune disorder, certain neurological disorders, or certain viral or fungal infections. Inflammatory disorders can include, e.g., osteoarthritis, rheumatoid arthritis (RA), spondyloarthropathies, POEMS syndrome, inflammatory bowel diseases (e.g., Crohn's disease or ulcerative colitis), multicentric Castleman's disease, systemic lupus erythematosus (SLE), Goodpasture's syndrome, multiple sclerosis (MS), polymyalgia rheumatica, muscular dystrophy (MD), polymyositis, dermatomyositis, inflammatory neuropathies such as Guillain Barré syndrome, vasculitis such as Wegener's granulomatosus, polyarteritis nodosa, polymyalgia rheumatica, temporal arteritis, Sjogren's syndrome, Behçet's disease, Churg-Strauss syndrome, or Takayasu's arteritis.

Various cytotoxic drugs can be included as part of a chemotherapy regimen. The particular cytotoxic agent or combination of agents, can depend on, e.g., the type of cancer and the severity of the cancer to be treated. For example, the subject can be administered one or more of any of a variety of cytoxic drugs including, without limitation, cyclophosphamide, taxol, methotrexate, nitrogen mustard, azathioprine, chlorambucil, fluorouracil, cisplatin, nocodazole, hydroxyurea, vincristine, vinblastine, etopiside, doxorubicin, bleomycin, carboplatin, gemcitabine, paclitaxel, topotecan, thioguanine, a therapeutic analog of any of the foregoing, and any other compounds that are known to result in decreased platelet counts (or decreased platelet production) in a subject.

Radiotherapy can involve, e.g., external beam radiotherapy (EBRT or XBRT), brachytherapy (or sealed-source radiotherapy), and unsealed-source radiotherapy, the difference being the position of the radiation source. "External" refers to a source of therapeutic radiation coming from outside the body, while sealed and unsealed source radiotherapy involves radioactive material administered internally to a subject. The type of radiation can be, e.g., X-ray or gamma-radiation. In some embodiments, the radiation therapy includes proton beam radiation therapy. "Internal" radiotherapy can be administered to a subject by way of infusion or ingestion. For example, metaiodobenzylguanidine (MIBG) infusion can be used to treat neuroblastoma. Iodine-131 can be administered orally to treat thyroid cancer or thyrotoxicosis. Hormones that are conjugated to lutetium-177 or yttrium-90 can be used to treat neuroendocrine tumors. Therapeutic antibodies can also be conjugated to radionuclides for use in radiotherapy. For example, non-Hodgkin's lymphoma can be treated using ibritumomab tiuxetan (Zevalin®), an anti-CD20 antibody conjugated to yttrium-90 and tositumomab iodine-131 (Bexxar®), an anti-CD20 antibody conjugated to iodine-131.

In some embodiments, the TPO mimetic antibody or fragment thereof can be administered to a subject who has undergone, or who is about to undergo, a bone marrow transplant, a surgery, and/or an autologous blood transfusion.

A TPO mimetic antibody, or a therapeutically-active fragment thereof, described herein can be used to treat a subject for radiation exposure. In some embodiments, the TPO mimetic antibody or fragment thereof can be administered to a subject following exposure to radiation. In some embodiments, a TPO mimetic antibody or fragment thereof can be administered to a subject likely to be exposed to radiation. As described above, a subject likely to be exposed to radiation can be, e.g.: a subject diagnosed with cancer and likely to undergo chemotherapy or radiotherapy; a subject likely to undergo a bone marrow transplant; or a subject likely to undergo surgery. A subject likely to be exposed to radiation can also be one who works at or near a facility that processes or uses radioactive materials. For example, a subject can be one who works at or near a nuclear power plant or a nuclear waste storage facility.

Suitable methods are also known in the art for determining the amount of radiation a subject has been exposed to. If the subject was wearing a monitoring device at the time of exposure and/or if a medical practitioner administers a known, therapeutically-effective dose of radiation, exposure calculations are greatly simplified. In the absence of a monitoring device, medical practitioners may require information about the exposure, such as intensity and type of radiation, duration of exposure, and distance from the source. Clinically, an immediate complete blood count with differential can be used to establish a hematologic baseline. Changes in the leukocytes and platelets occur over a period of days to weeks. The severity of these changes can also be used to approximate the exposure. For example, whole-body radiation exposures in excess of 100 Rad (1 Gray) can result in a decrease in the circulating level of lymphocytes. This decrease can be observed within the first 24 hours after exposure. Because the amount of decrease is proportional to the severity of exposure, the lymphocytes can be used as a biologic dosimeter.

In view of the efficacy of the TPO mimetic antibodies and therapeutically-active fragments described herein, they can be administered to a subject as a single dose. (See working Examples.) The efficacy of single dose therapy using TPO mimetic peptides in humans has been described in, e.g., Wang et al. (2004) *Clin Pharm Ther* 76:628-638 and Kuter et al. (2009) *Annu Rev Med* 60:33.11-33.141 (published online ahead of print on Oct. 31, 2008).

In some embodiments, the TPO mimetic antibodies or fragments can be administered to a subject as more than one (e.g., two, three, four, five, six, seven, eight, nine, 10, or 15 or more) dose(s). In multi-dose embodiments, dosing can be, e.g., daily, once every two days, twice per week, weekly, biweekly, or once per month. For example, a subject can be administered a TPO mimetic antibody once per day for at least five days. In another example, a subject can be administered a TPO mimetic antibody once per day for three days. As described above, the administration can occur prior to, during, and/or following exposure to a platelet count-decreasing event such as radiation exposure or chemotherapy. In some embodiments, e.g., a subject can be administered a single dose of a TPO mimetic, or fragment thereof, about one day (e.g., about 20 hours, about 24 hours, or about 30 hours) prior to exposure to radiation or undergoing a chemotherapy regimen.

In some embodiments, a subject can be administered a TPO mimetic antibody, or therapeutically-active fragment thereof, less than one (1) day (e.g., less than 23, 22, 21, 20, 19, 18, 17, 16, 15, 14, 13, 12, 11, 10, nine, eight, seven, six, five, four, three, two, one, or less than one hour) prior to, or after, exposure to radiation (e.g., a radiotherapy regimen) or undergoing a chemotherapy regimen. For example, a subject can be administered a single dose of the TPO mimetic antibody, or a therapeutically-active fragment thereof, 6 or 12 hours prior to exposure to radiation.

In another example, a subject can be administered a single dose of the TPO mimetic antibody, or a therapeutically-active fragment thereof, 6, 12, or 24 hours after exposure to radiation.

In some embodiments, a TPO mimetic antibody, or therapeutically-active fragment thereof, described herein can be subcutaneously administered to a human subject once per week for six (6) consecutive weeks at a dose of at least 3 (e.g., at least 4, 5, 6, 7, 8, 9, or 10) µg/kg of the subject. See, e.g., Bussel et al. (2006) *N Engl J Med* 355:1672-1681. In some embodiments, a TPO mimetic antibody, or therapeutically-active fragment thereof, described herein can be subcutaneously administered to a human subject once per week for two (2) consecutive weeks at a dose of at least 0.2 to 10 µg/kg of the subject (see, e.g., Wang et al. (2004), supra). In some embodiments, a TPO mimetic antibody, or therapeutically-active fragment, described herein can be intravenously administered to a human subject at a dose of about 0.3 to 10 (e.g., about 0.5 to 5, 1.0 to 10, 2.0 to 5, 6 to 10, 6 to 8, 9 to 10, 1 to 4, 2 to 4, 0.3 to 1.0, 0.3 to 3, 0.5 to 2, or 0.7 to 7) µg/kg of the subject. See, e.g., Wang et al. (2004), supra.

Likewise, any therapeutic antibody, or therapeutically-active fragment thereof, can be administered as a single dose. In some embodiments, the therapeutic antibodies, or their fragments, can be administered to a subject as more than one (e.g., two, three, four, five, six, seven, eight, nine, 10, or 15 or more) dose(s). In multi-dose embodiments, dosing can be, e.g., daily, once every two days, twice per week, weekly, biweekly, or once per month.

In some embodiments, a particular dosing regimen may be altered, e.g., if the therapeutic antibody is discovered to elicit an immune response in a treated subject. In fact, a doctor, nurse, or other authorized medical practitioner may monitor a treated subject for the production of antibodies that specifically bind to and/or inhibit the therapeutic activity of the therapeutic antibody. In such a case, a medical practitioner may elect to stop administering the therapeutic antibody to the subject and/or elect to administer a different therapeutic antibody to the subject. For example, if a treated subject is discovered to produce antibodies that bind to a particular TPO mimetic peptide within a first TPO mimetic antibody, a medical practitioner may elect (where reagents are available) to administer to the subject a different TPO mimetic antibody that contains a different TPO mimetic that is not expected to bind to the subject's antibodies. In another example, if a treated subject is discovered to produce antibodies that bind to an epitope of a particular scaffold antibody of a first TPO mimetic antibody, a medical practitioner may elect (where reagents are available) to administer to the subject a different TPO mimetic antibody that is built around a different antibody scaffold that is not expected to bind to the subject's antibodies. Methods for detecting the production by a subject (e.g., a human subject) of neutralizing antibodies that bind to and inhibit the activity of a therapeutic antibody are known in the art and described in, e.g., Welt et al. (2003) *Clin Cancer Res* 9(4):1338-46; Szolar et al. *J Pharm Biomed Anal* 41(4):1347-1353; and Lofgren et al. (2007) *J Immunol* 178(11):7467-7472.

In some embodiments, the therapeutic antibody (e.g., the TPO mimetic antibody), or therapeutically-active fragment thereof, can be administered to a subject as a monotherapy. Alternatively, as described above, the antibody or fragment can be administered to a subject as a combination therapy with another treatment, e.g., another treatment for increasing platelet production in a subject or for treating a subject for radiation exposure. For example, the combination therapy can include administering to the subject (e.g., a human patient) one or more additional agents (e.g., eltrombopag, oprelvekin, or romiplostim) that provide a therapeutic benefit to the subject in need thereof. In some embodiments, the therapeutic antibody (e.g., the TPO mimetic antibody), or a therapeutically-active fragment thereof, and the one or more additional active agents are administered at the same time. In other embodiments, the antibody or fragment is administered first in time and the one or more additional active agents are administered second in time. In some embodiments, the one or more additional active agents are administered first in time and the antibody or fragment is administered second in time.

The therapeutic antibody (e.g., the TPO mimetic antibody), or therapeutically-active fragment thereof, can replace or augment a previously or currently administered therapy. For example, upon treating with the TPO mimetic antibody or therapeutically-active fragment thereof, administration of the one or more additional active agents (e.g., eltrombopag, oprelvekin, or romiplostim) can cease or diminish, e.g., be administered at lower levels. In some embodiments, administration of the previous therapy can be maintained. In some embodiments, a previous therapy will be maintained until the level of the therapeutic antibody, or therapeutically-active fragment thereof, reaches a level sufficient to provide a therapeutic effect. The two therapies can be administered in combination.

As described above, in some embodiments, a subject can be monitored for an increase in platelet production (or an increase in platelet levels) following a treatment. In some embodiments, a subject can be monitored for an improvement in one or more symptoms of radiation exposure following treatment with a TPO mimetic antibody or fragment thereof. Such symptoms vary according to the type of radiation to which a subject is exposed, the dose of the radiation, and the location of the exposure. The symptoms are known in the art and include, e.g., malaise, pain, sore throat, gastrointestinal distress (vomiting and/or diarrhea), epilation, loss of appetite, burns, and hemorrhage. Monitoring a subject (e.g., a human patient) for an improvement in a disorder related to insufficient platelet counts, as defined herein, means evaluating the subject for a change in a disease parameter, e.g., an improvement in one or more symptoms of the disorder. Such symptoms vary depending on the particular disorder, but are well known in the art of medicine. See, e.g., Harker and Zimmerman (1983) "Platelet Disorders," Saunders, 360 pages; and Gresele et al. (2002) "Platelets in Thrombotic and Non-thrombotic Disorders: Pathophysiology, Pharmacology and Therapeutics," Cambridge University Press (ISBN 052180261X).

In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning the treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for radiation exposure or increasing platelet production in a subject, as described herein.

Ex Vivo Approaches.

An ex vivo strategy for increasing platelet production in a subject can involve transfecting or transducing one or more cells obtained from a subject with a polynucleotide encoding a therapeutic antibody (e.g., a TPO mimetic antibody), or a therapeutically-active fragment thereof, described herein. For example, the cells can be transfected with a single vector encoding a heavy and light chain of a TPO mimetic antibody or the cells can be transfected with a first vector encoding a heavy chain and a second vector encoding a light chain of the antibody. In some embodiments, the vector contains an inducible promoter that allows a medical practitioner to turn on, or turn off, production of the TPO mimetic antibody (or fragment) in a subject. For example, a medical practitioner may elect to turn on expression of a TPO mimetic antibody described herein in a patient scheduled to undergo a second round of a radiation therapy regimen. Following the regimen and recovery of platelet levels in the subject, the medical practitioner can elect to turn off expression of the antibody in the subject.

The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells can act as a source (e.g., sustained or periodic source) of the therapeutic antibody (e.g., the TPO mimetic antibody), or the therapeutically-active fragment thereof, for as long as they survive in the subject. In some embodiments, the vectors and/or cells can be configured for inducible or repressible expression of the antibody (see, e.g., Schockett et al. (1996) *Proc. Natl. Acad. Sci. USA* 93:5173-5176 and U.S. Pat. No. 7,056,897).

Preferably, the cells are obtained from the subject (autologous), but can potentially be obtained from a subject of the same species other than the subject (allogeneic).

Suitable methods for obtaining cells from a subject and transducing or transfecting the cells are known in the art of molecular biology. For example, the transduction step can be accomplished by any standard means used for ex vivo gene therapy, including calcium phosphate, lipofection, electroporation, viral infection (see above), and biolistic gene transfer. See, e.g., Sambrook et al. (supra) and Ausubel et al. (supra). Alternatively, liposomes or polymeric microparticles can be used. Cells that have been successfully transduced can be selected, for example, for expression of the coding sequence or of a drug resistance gene.

In some embodiments, a biological sample containing megakaryocytes can be obtained from a subject and contacted with a TPO mimetic antibody to promote the production of platelets. The treated biological sample can then be reintroduced into the subject or to another subject of the same species as the subject. Such ex vivo autologous or allogeneic transplantation methods can be useful for restoring platelet levels in a subject who has received, or who is receiving, radiotherapy or chemotherapy. In such cases, the biological sample is removed in advance of the radiotherapy or chemotherapy.

Kits

The disclosure also features articles of manufacture or kits, which include a container with a label; and a composition containing a therapeutic antibody (e.g., a TPO mimetic antibody), or therapeutically-active fragment thereof described herein. Where the composition contains a TPO mimetic antibody, or a therapeutically-active fragment thereof, the label can indicate that the composition is for use in increasing platelet production in a subject in need thereof and/or to be administered to a subject (e.g., a human) in connection with chemotherapy or radiotherapy. The kit can, optionally, include a means for administering the composition to the subject. For example, the kits can include one or more syringes. The kits can also optionally include instructions for administering the composition to a subject.

In some embodiments, the kits can further include one or more additional active agents for increasing platelet production in a subject. For example, the kits can include one or more of Promacta®/Revolade® (eltrombopag; GlaxoSmithKline), Neumega® (oprelvekin; rhIL-11, Genetics Institute, Inc.), Nplate™ (romiplostim; Amgen, Inc.), and any other of active agents described herein. In some embodiments, the kits can include one or more active agents for treating a subject for radiation exposure. For example, the kits can include one or more of an antibiotic, an anesthetic, an antiemetic, a steroid (e.g., an androstenediol such as 4-androstenediol or 5-androstenediol), a chelating agent, a diuretic, a radionuclide-displacing agent, and a stem cell.

The kit can optionally include one or more reagents for determining the platelet levels in a blood sample obtained from a subject. The kit can also include one or more reagents for collecting a blood sample from a subject.

The following examples are intended to illustrate, not limit, the invention.

EXAMPLES

Example 1

Reagents

The following reagents were used in the experiments described below:

(1) recombinant human thrombopoietin (hereinafter referred to as "rhTPO");

(2) a composition containing a humanized anti-complement component C5 antibody (5G1.1) scaffold in which CDR3 of the heavy chain is replaced with a TPO mimetic peptide (hereinafter referred to as "CDR-TPO antibody"); the antibody no longer binds to C5; the heavy chain constant region is a G2/G4 constant region fusion as described above;

(3) a composition containing a humanized anti-complement component C5 antibody (5G1.1) that does not contain a TPO mimetic peptide (hereinafter referred to as "anti-C5 control antibody"); the heavy chain constant region is a G2/G4 constant region fusion as described above;

(4) a composition containing a F(ab')$_2$ fragment of an anti-tetanus toxoid antibody in which CDR3 of the heavy chain contains a TPO mimetic peptide and CDR2 of the light chain contains a TPO mimetic peptide (hereinafter referred to as "TPO-Fab");

(5) a TPO mimetic antibody having a human anti-anthrax antibody scaffold, wherein the light chain polypeptides contain a TPO mimetic at the carboxy-terminus (hereinafter referred to as "LC-TPO antibody"); the heavy chain constant region is a G2/G4 constant region fusion as described above; and the antigen combining sites of the antibody bind to the pA83 antigen of Bacillus anthracis;

(6) a TPO mimetic antibody having a human anti-anthrax antibody scaffold, wherein the heavy chain polypeptides contain a TPO mimetic inserted slightly beyond the carboxy-terminal end of the heavy chain hinge region (hereinafter referred to as "HC-TPO antibody"), the TPO mimetic being inserted between the 5$^{th}$ and 6$^{th}$ residues of the CH2 portion of the anti-anthrax antibody scaffold; the heavy chain constant region is a G2/G4 constant region fusion as described above; and the antigen combining sites of the antibody bind to the PA83 antigen of Bacillus anthracis;

(7) a TPO mimetic antibody having a human anti-anthrax antibody scaffold, wherein the light chain polypeptides contain a TPO mimetic at the carboxy-terminus and the heavy chain polypeptides contain a TPO mimetic inserted slightly beyond the carboxy-terminal end of the heavy chain hinge region (hereinafter referred to as "HC+LC-TPO antibody"); the heavy chain constant region is a G2/G4 constant region fusion as described above; and the antigen combining sites of the antibody bind to the PA83 antigen of Bacillus anthracis;

(8) a human anti-anthrax antibody that does not contain a TPO mimetic and the heavy chain constant region contained a G2/G4 constant region fusion as described above (hereinafter referred to as "the anti-anthrax G2/G4 control antibody"); and the antigen combining sites of the antibody bind to the PA83 antigen of Bacillus anthracis; and (9) a human anti-anthrax antibody that does not contain a TPO mimetic, wherein the heavy chain constant region is a G1 constant region (hereinafter referred to as "anti-anthrax G1 control antibody") and wherein and the antigen combining sites of the antibody bind to the PA83 antigen of Bacillus anthracis.

Example 2

Generation and Purification of the HC+LC-TPO Antibody

A plasmid expression vector was generated using standard molecular biology techniques, which vector contains a nucleic acid encoding the light chain and the heavy chain of the HC+LC-TPO antibody described above. The vector was transfected into CHOK1SV cells, a Chinese Hamster Ovary cell line, by electroporation. The transfectants were screened for clones that stably expressed the antibody. A clone was selected and used to produce a large scale culture for production and purification of a therapeutic antibody.

Purification

The HC+LC-TPO antibody was purified from cell culture supernatant (900 mL) using a protein A (POROS®) resin. Prior to passing the supernatant over the column, the column was first equilibrated with eight column volumes of an equilibration buffer (250 mM NaCl, 50 mM glycine, pH 8). Following column equilibration, the supernatant was loaded onto the column at a flow rate of 9 mL/min. Once the sample was loaded onto the column, the column was washed with the equilibration buffer until the UV absorbance at 280 nm had returned to zero. The antibody was eluted from the column with 150 mM NaCl, 100 mM glycine, pH 3.5 and the peak fraction was manually collected. The peak fraction was neutralized with 1 M Tris pH 9, and dialyzed into phosphate buffered saline.

Following dialysis, the sample was filtered through a 0.22 μm Sterivex filter (Millipore), and the concentration determined by UV spectroscopy at 280 nm wavelength. Purified antibody was tested for endotoxin contamination using a QCL-1000 chromogenic LAL endpoint assay kit (Lonza).

Example 3

In Vitro Functional Characterization of the HC+LC-TPO Antibody

Recombinant TPO receptor (R&D Systems®; Minneapolis, Minn.) was biotinylated at a 1:1 ratio of biotin:protein using No-Weigh™ Biotin (Thermo Scientific/Pierce). The biotinylated TPO receptor (5 μg/mL) was coupled to a streptavidin probe for 15 minutes. The probe was washed and subsequently contacted with 25 nM of the HC+LC-TPO antibody. The association and dissociation of the antibodies to the probe were monitored by Octet QK (Forté-Bio10; Menlo Park, Calif.) over 15 minutes. The binding kinetics between the two proteins were determined using partial fitting in conjunction with Forté-Bio® analysis software. The $K_D$ was determined to be approximately 2.32 nM.

A similar experiment was also performed using the above described biotinylated TPO receptor and streptavidin probe, wherein the probe was contacted with the HC+LC-TPO antibody or rhTPO. In this experiment, for each of the HC+LC-TPO antibody and rhTPO, the $K_D$ was determined to be approximately 3 nM. These results show that the affinity for the TPO mimetic antibody for the TPO receptor was the same as the affinity for rhTPO for the receptor.

Example 4

Effect of a TPO Mimetic on Platelet Counts in Mice

Balb/c mice, 13 weeks of age, were treated with a rhTPO, TPO-Fab, the CDR-TPO antibody, or the anti-C5 control antibody, as described above in Example 1. Five mice were treated in each group. The compositions were administered to the mice by subcutaneous injection once a day for five consecutive days at a dosage of 2 mg/kg of CDR-TPO or control antibody, 13.3 mg/kg TPO-Fab, or 110 µg/kg rhTPO. 100 µL of blood from each mouse was obtained on days 3, 5, 8, 10, and 12, day 1 being the first treatment. Peripheral blood platelets in the blood were measured using a Cell-Dyn™ 3100 Hematology Analyzer (Abbott Diagnostics, Ill.).

As shown in FIG. 1, platelet levels were substantially increased in mice treated with rhTPO, the CDR-TPO antibody, and TPO-Fab, as compared to the control antibody.

Example 5

Effect of a TPO Mimetic Antibody on Platelet Counts in Mice

Balb/c mice, 13 weeks of age, were treated with the CDR-TPO antibody, the anti-anthrax G1 control antibody, the HC-TPO antibody, the LC-TPO antibody, or the HC+LC-TPO antibody. The antibodies are described above in Example 1.

Five mice were in each treatment group. The antibodies were administered to the mice by subcutaneous injection once a day for five consecutive days at a dosage of 2 mg/kg. 100 µL of blood from each mouse was obtained on days 0, 4, 7, 9, 11, 16, and 18, day 1 being the first treatment. Peripheral blood platelets in the blood were measured as described above.

Figure 2:
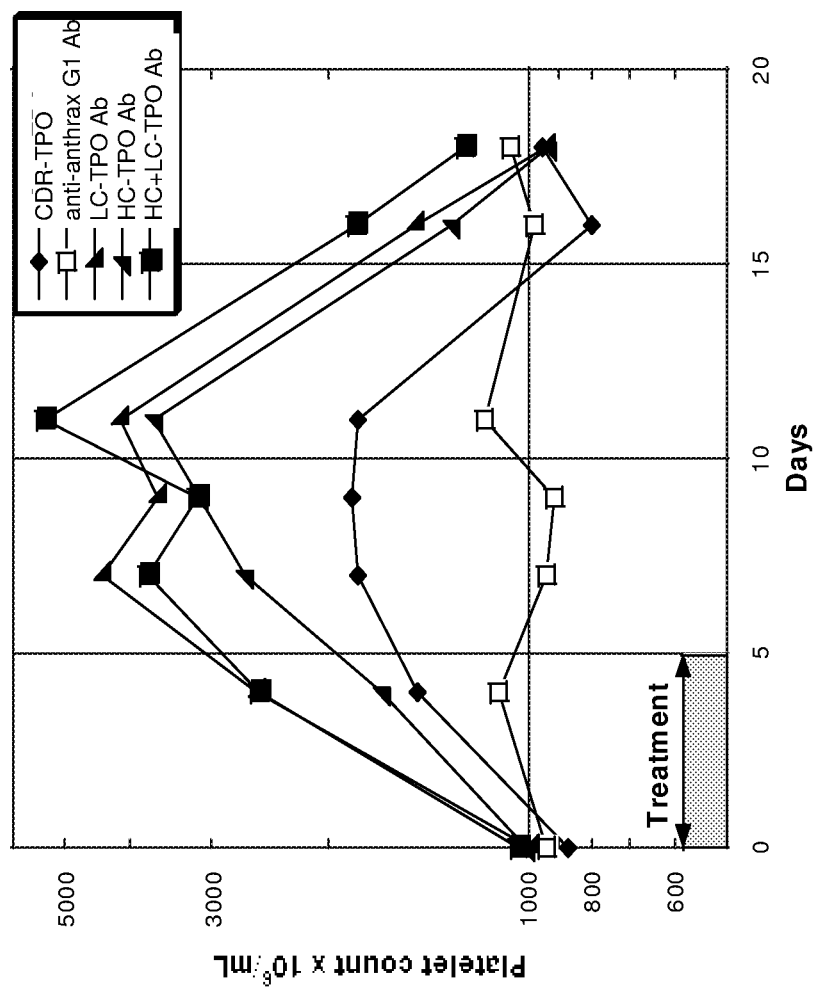

As shown in FIG. 2, platelet levels were increased in mice treated with any of the TPO mimetic antibodies, as compared to the anti-anthrax G1 control antibody. Moreover, platelet levels obtained in mice treated with the HC-TPO antibody, the LC-TPO antibody, or the HC+LC-TPO antibody were substantially higher than the platelet levels obtained in mice treated with the CDR-TPO antibody. For example, at day 11, platelet levels obtained with the HC+LC-TPO antibody ($5,375 \times 10^6$ platelets/mL) were nearly three times higher than the corresponding platelet levels in mice treated with CDR-TPO antibody ($1,802 \times 10^6$ platelets/mL). These results demonstrated that, surprisingly, the antibodies having a TPO mimetic at the carboxy-terminus of the light chain and/or the heavy chain hinge region were even more effective at raising platelet levels in animals than antibodies containing TPO mimetic peptides in the CDR regions.

In addition, platelet levels increased more quickly in mice treated with, e.g., the LC-TPO antibody and the HC+LC-TPO antibody as compared to the CDR-TPO antibody (see platelet levels at day 4; FIG. 2).

Several other CDR-TPO mimetic constructs were tested for their ability to stimulate platelet production in a mouse using the above-described method. The antibodies contained two or four TPO mimetics, which were inserted into the CDRs of the heavy chain and/or light chain variable regions. For example, one antibody contained two heavy chain polypeptides in which CDR3 had been replaced with a TPO mimetic and two light chain polypeptides in which the CDR2 had been replaced with a TPO mimetic. Another antibody contained two heavy chain polypeptides in which CDR3 had been replaced with a TPO mimetic and two light chain polypeptides in which the CDR1 had been replaced with a TPO mimetic. None of these antibodies was as potent at raising platelet levels in a mouse as the HC-TPO antibody, the LC-TPO antibody, or the HC+LC-TPO antibody.

Taken together, these data demonstrate that the HC-TPO antibody, the LC-TPO antibody, and the HC+LC-TPO antibody are more effective in eliciting greater total platelet production, as well as quicker platelet production, in an animal, than the CDR-TPO counterpart antibody molecules. These data also suggest that the particular placement of the TPO mimetic peptides in one or both of the carboxy-terminus of the light chain (allowing presentation of the mimetic at the central cleft of the antibody) and at or near to the hinge region of the heavy chain affords a superior TPO-like biological activity to the LC-TPO antibody, the HC-TPO antibody, and the HC+LC-TPO antibody.

Example 6

Effect of Single Dose TPO Mimetic Antibody Treatment on Platelet Counts in Mice

Figure 3:
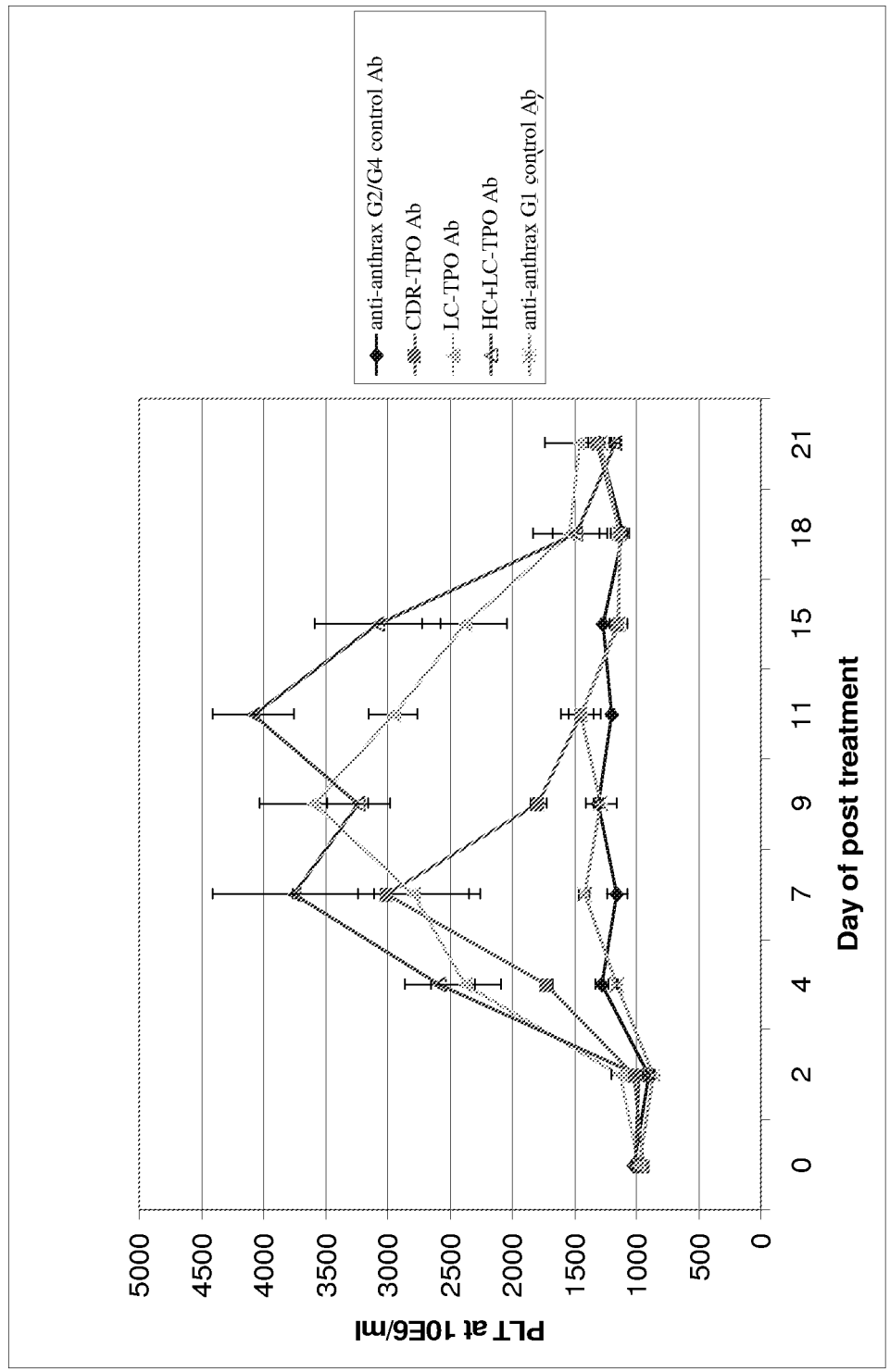

Balb/c mice, 14 weeks of age, were treated with the anti-anthrax G1 control antibody, the CDR-TPO antibody, the LC-TPO antibody, the HC+LC-TPO antibody, and the anti-anthrax G2/G4 control antibody. There were three (3) mice in each treatment group. The antibodies were administered to the mice by subcutaneous injection one (1) time at a dosage of 2 mg/kg. Blood was collected from each mouse at days 0, 2, 4, 7, 9, 11, 15, 18, and 21 with respect to the treatment. Peripheral blood platelets were analyzed as described above. As shown in FIG. 3, platelet levels were increased in mice treated with the LC-TPO antibody or HC+LC-TPO antibody, as compared to the platelet levels in mice treated with the anti-anthrax control antibodies. Again, these data demonstrated that platelet levels obtained in mice treated with the LC-TPO antibody or HC+LC-TPO antibody were substantially higher than the platelet levels obtained in mice treated with the CDR-TPO antibody. The data also demonstrated that the LC-TPO antibody and the HC+LC-TPO antibody were more capable of maintaining elevated platelet levels in the blood of animals, as compared to the CDR-TPO antibody. (See, e.g., days 9 to 15, FIG. 3).

Moreover, these data also demonstrated that, surprisingly, a single dose of the LC-TPO antibody or HC+LC-TPO antibody was not only capable of substantially increasing platelet levels in mice, but that the single dose was nearly as effective as the multi-dosing schedule (compare to FIG. 2).

Example 7

Effect of TPO Mimetic Antibodies on Platelet Levels in MMC-Treated Mice

Balb/c mice, 14 weeks of age, were intravenously administered mitomycin C (MMC) at a dose of 3 mg/mL. Following the MMC treatment, the above-described CDR-TPO antibody or the anti-C5 control antibody was also administered to the mice by subcutaneous injection once per day for five consecutive days at a dosage of 600 µg/kg. Blood was collected from the treated mice, as well as from sham control mice, on days 8, 11, 15, 18, 21, 25, and 32 after the MMC treatment (day 0). Peripheral blood platelets in the blood were measured as described above.

Figure 4:
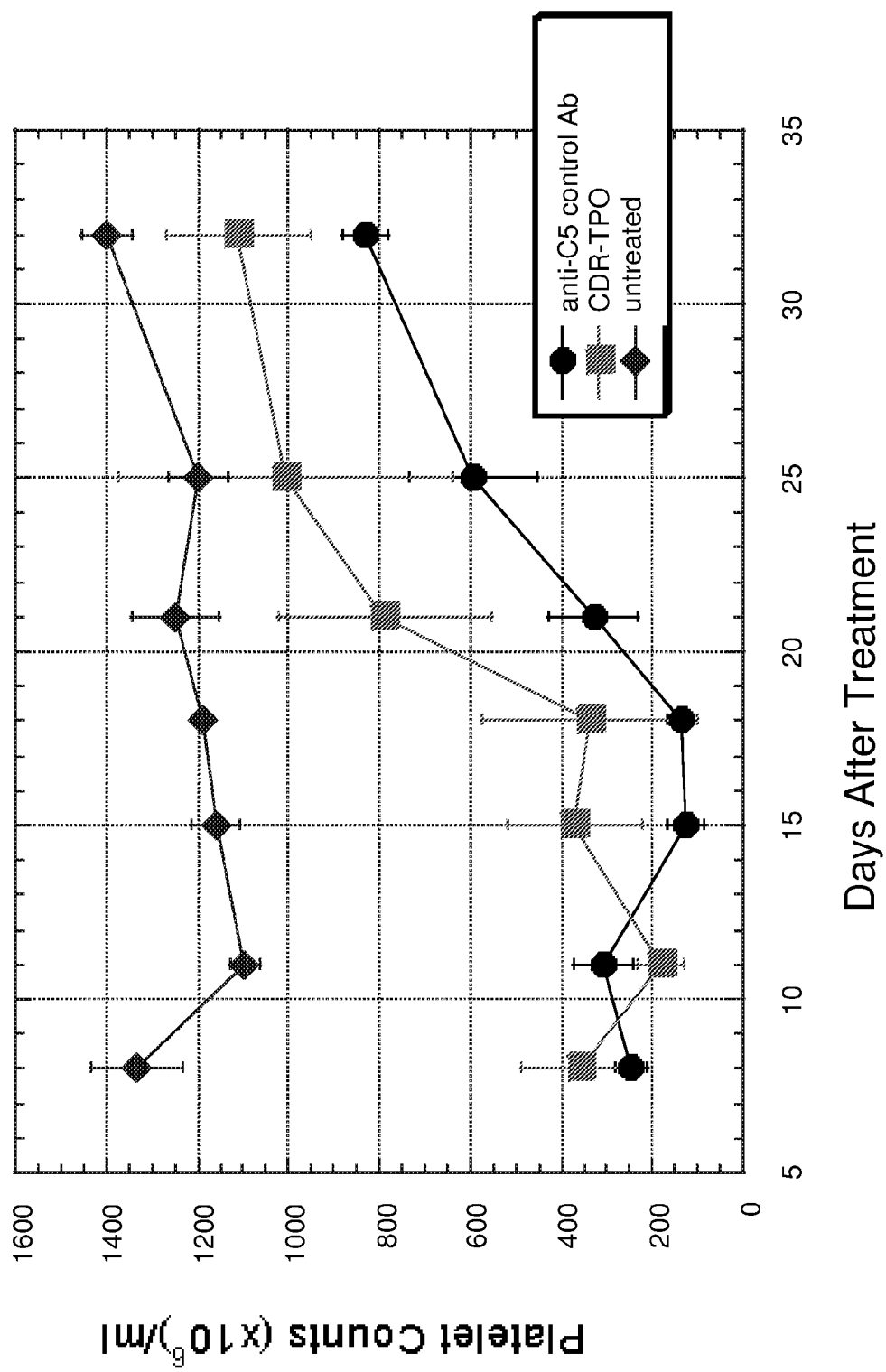

As is shown in FIG. 4, platelet levels were increased in mice treated with the CDR-TPO antibody as compared to mice treated with the anti-C5 control antibody. These results indicate that the CDR-TPO antibody is effective in animals for more quickly recovering platelet levels following a myelosuppressive therapy as compared to no treatment with an agent that increases platelet production.

Based on the results of the above-described experiments using the LC-TPO antibody, HC-TPO antibody, and HC+LC-TPO antibody, it is expected that these antibodies will be effective in animals for recovering platelet levels following a myelosuppressive therapy. In addition, the previous results also suggest that the LC-TPO antibody, HC-TPO antibody, and HC+LC-TPO antibody would be equal to, or more effective than, the CDR-TPO antibody in the recovery of platelets.

An experiment to test this assumption is as follows. Balb/c mice, 14 weeks of age, are intravenously administered mitomycin C (MMC) at a dose of 3 mg/mL. Following the MMC treatment, the mice are also administered by subcutaneous injection one of the following antibodies: the CDR-TPO antibody, the LC-TPO antibody, the HC-TPO antibody, the HC+LC-TPO antibody, the anti-C5 control antibody, the anti-anthrax G1 control antibody, and the anti-anthrax G2/G4 control antibody.

The antibodies are administered once per day for five consecutive days at a dose of 2 mg/kg. Blood is collected from each mouse at days 0, 2, 4, 7, 9, 11, 15, 18, and 21 following MMC treatment (day 0). Peripheral blood platelets are analyzed as described above. Platelet levels are expected to be increased in mice treated with each of the two TPO mimetic antibodies and the CDR-TPO antibody, as compared to the control antibodies. These data will indicate that the LC-TPO antibody, the HC-TPO antibody, and the HC+LC-TPO antibody are effective in animals for recovering platelet levels following a myelosuppressive therapy. Moreover, the data are expected to show that the LC-TPO antibody, the HC-TPO antibody, or the HC+LC-TPO antibody will raise platelet levels more quickly and will sustain the platelet levels longer in animals than will the CDR-TPO antibody.

In another experiment, Balb/c mice, 14 weeks of age, are administered by subcutaneous injection one of the following antibodies: the CDR-TPO antibody, the LC-TPO antibody, the HC-TPO antibody, the HC+LC-TPO antibody, the anti-C5 control antibody, the anti-anthrax G1 control antibody, and the anti-anthrax G2/G4 control antibody. The antibodies are administered under the following dosing regimens. The first treatment regimen involves administering the antibodies to the mice once per day for five consecutive days at a dose of 600 µg/kg. One day after the final dose, the mice are intravenously administered mitomycin C (MMC) at a dose of 3 mg/mL. The second treatment regimen involves administering to the mice a single 600 µg/kg dose of the antibody three days prior to MMC treatment. The third treatment regimen involves administering to the mice a single 600 µg/kg dose of the antibody one day prior to MMC treatment. It is expected that there will be increased platelet levels in mice treated with the LC-TPO antibody, the HC-TPO antibody, or the HC+LC-TPO antibody as compared to the platelet levels in mice that are treated with the anti-anthrax or anti-C5 control antibodies. It is also expected that the single dose of the LC-TPO antibody, the HC-TPO antibody, or the HC+LC-TPO antibody administered to mice prior to MMC treatment will substantially increase the platelet levels in subsequently MMC-treated mice.

In yet another experiment, Balb/c mice, 14 weeks of age, are administered by subcutaneous injection one of the following antibodies: the CDR-TPO antibody, the LC-TPO antibody, the HC-TPO antibody, the HC+LC-TPO antibody, the anti-C5 control antibody, the anti-anthrax G1 control antibody, and the anti-anthrax G2/G4 control antibody. The antibodies are administered under the following dosing regimens. The first treatment regimen involves administering the antibodies to the mice once per day for five consecutive days at a dose of 600 µg/kg. One day before the first dose, the mice are intravenously administered mitomycin C (MMC) at a dose of 3 mg/mL. The second treatment regimen involves administering to the mice a single 600 µg/kg dose of the antibody one day after the MMC treatment. The third treatment regimen involves administering to the mice a single 600 µg/kg dose of the antibody three days after the MMC treatment. It is expected that there will be increased platelet levels in mice treated with the LC-TPO antibody, the HC-TPO antibody, or the HC+LC-TPO antibody as compared to the platelet levels in mice that are treated with the anti-anthrax or anti-C5 control antibodies. It is also expected that the single dose of the LC-TPO antibody, the HC-TPO antibody, or the HC+LC-TPO antibody administered to mice just after the MMC treatment will substantially increase the platelet levels in subsequently MMC-treated mice.

Together, these findings will further support the conclusion that the particular placement of the TPO mimetic peptides in one or both of the carboxy-terminus of the light chain (allowing presentation of the TPO mimetic at the central cleft of the antibody) and at or near the hinge region of the heavy chain affords a superior TPO-like biological activity to these TPO mimetic antibody molecules.

Therefore, the LC-TPO antibody, the HC-TPO antibody, and the HC+LC-TPO antibody are expected to be useful for treating animals undergoing a myelosuppressive therapy.

Example 8

Effect of TPO Mimetic Antibodies on Platelet Levels in Gamma-Irradiated Mice (Pre-Treatment)

C57BL6/J mice, 8-10 weeks of age, are administered by subcutaneous injection one of the following antibodies: the CDR-TPO antibody, the LC-TPO antibody, the HC-TPO antibody, the HC+LC-TPO antibody, the anti-C5 control antibody, the anti-anthrax G1 control antibody, and the anti-anthrax G2/G4 control antibody.

The antibodies are administered under three treatment regimens. The first treatment regimen involves administering the antibodies to the mice once per day for five consecutive days at a dose of 2 mg/kg. One day after the final dose, the mice are subjected to 8.0 Gray (Gy) radiation at approximately 0.90 Gy/minute as described in Mouthon et al. (1999) *Int. J Radiation Oncology Biol Phys* 43(4):867-875. The second treatment regimen involves administering to the mice a single 2 mg/kg dose of the antibodies three days prior to irradiation. The third treatment regimen involves administering to the mice a single 2 mg/kg dose of the antibodies one day prior to irradiation. The survival of the treated mice is monitored over 30 days after irradiation.

It is expected that there will be increased survival of irradiated mice treated with the LC-TPO antibody, the HC-TPO antibody, or the HC+LC-TPO antibody as compared to the survival of mice that are treated with the anti-anthrax or anti-C5 control antibodies. It is also expected that the single dose of the LC-TPO antibody, the HC-TPO antibody, or the HC+LC-TPO antibody administered to mice prior to irradiation will substantially increase the survival of irradiated mice.

Moreover, it is expected that the LC-TPO antibody, the HC-TPO antibody, or the HC+LC-TPO antibody will be more effective at increasing the survival of irradiated mice than antibodies that contain the TPO mimetics in the CDR region.

Example 9

Effect of TPO Mimetic Antibodies on Platelet Levels in Gamma-Irradiated Mice (Post-Treatment)

In another experiment, C57BL6/J mice, 8-10 weeks of age, are administered by subcutaneous injection one of the following antibodies: the CDR-TPO antibody, the LC-TPO antibody, the HC-TPO antibody, the HC+LC-TPO antibody, the anti-C5 control antibody, the anti-anthrax G1 control antibody, and the anti-anthrax G2/G4 control antibody.

Under one treatment regimen, the antibodies are administered to the mice 6 hours after exposure to 8.0 Gray (Gy) radiation at approximately 0.90 Gy/minute as described in Mouthon et al. (1999), supra. In the second treatment regimen, the antibodies are administered to the mice at 6 hours, and once per day for four consecutive days, following irradiation of the mice. The survival of the treated mice is monitored over 30 days after irradiation. It is expected that there will be increased survival of irradiated mice treated with the LC-TPO antibody, the HC-TPO antibody, or the HC+LC-TPO antibody as compared to the survival of mice that are treated with the anti-anthrax or anti-C5 control antibodies. It is also expected that a single dose of the LC-TPO antibody, the HC-TPO antibody, or the HC+LC-TPO antibody administered after irradiation will substantially increase the survival of irradiated mice as compared to the survival of mice treated with control antibodies.

Moreover, it is expected that the LC-TPO antibody, the HC-TPO antibody, or the HC+LC-TPO antibody will be more effective at increasing the survival of irradiated mice than antibodies that contain the TPO mimetics in the CDR region.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A polypeptide which comprises:
   (i) a light chain polypeptide comprising the amino acid sequence depicted in SEQ ID NO: 10;
   (ii) a heavy chain polypeptide comprising the amino acid sequence depicted in SEQ ID NO: 12; or
   (iii) a light chain polypeptide comprising the amino acid sequence depicted in SEQ ID NO: 10 and a heavy chain polypeptide comprising the amino acid sequence depicted in SEQ ID NO: 12.

2. An isolated polypeptide comprising an amino acid sequence that comprises at least one thrombopoietin (TPO) mimetic peptide amino acid sequence and is:
   (i) at least 95% identical to the amino acid sequence depicted in SEQ ID NO: 10; or
   (ii) at least 95% identical to the amino acid sequence depicted in SEQ ID NO: 12.

3. A composition comprising the polypeptide of claim 1 or 2, and a pharmaceutically acceptable carrier.

4. The polypeptide of claim 1 or 2, wherein the polypeptide is selected from the group consisting of a monoclonal antibody, a humanized antibody, a chimerized antibody, a chimeric antibody, a deimmunized human antibody, and a fully human antibody.

5. The polypeptide of claim 2, wherein the TPO mimetic comprises the amino acid sequence of SEQ ID NO: 1.

6. A method for increasing platelet production in a subject, the method comprising administering to a subject in need thereof a composition comprising a therapeutically-effective amount of the polypeptide of claim 1 or 2.

7. The method of claim 6, wherein the subject has a disorder related to insufficient platelet counts or a cancer.

8. The method of claim 7, wherein the disorder is selected from the group consisting of Bernard-Soulier syndrome, idiopathic thrombocytopenic purpura, Wiskott-Aldrich syndrome, hypersplenism, thrombotic microangiopathies, disseminated intravascular coagulation, heparin-induced thrombocytopenia (HIT), von Willebrand disease, variant von Willebrand disease, thrombocytopenia resulting from HIV infection, thrombocytopenia resulting from chronic liver disease, a drug-induced platelet insufficiency, and Glanzmann's thrombasthenia.

9. The method of claim 6, wherein the subject is a human.

10. The method of claim 6, wherein the polypeptide is administered to the subject:
    (i) prior to and during or following the chemotherapy or the radiotherapy regimen;
    (ii) prior to the chemotherapy or the radiotherapy regimen; or
    (iii) during or following the chemotherapy or the radiotherapy regimen.

11. The method of claim 6, wherein the chemotherapy or radiotherapy regimen is (i) more potent or (ii) administered more frequently to a subject than would be safely possible in the absence of administering the polypeptide.

* * * * *

```
                              SEQUENCE LISTING

<160> NUMBER OF SEQ ID NOS: 16

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide mimetic sequence

<400> SEQUENCE: 1

Ile Glu Gly Pro Thr Leu Arg Gln Trp Leu Ala Ala Arg Ala
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimetic sequence

<400> SEQUENCE: 2

Ile Glu Gly Pro Thr Leu Arg Gln Trp Leu Ala Ala Arg Ala Pro
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide mimetic sequence

<400> SEQUENCE: 3

Asp Tyr His Cys Arg Met Gly Pro Leu Thr Trp Val Cys Lys Pro Leu
```

```
1               5                   10                  15
Gly Gly

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide mimetic

<400> SEQUENCE: 4

Ala Phe Leu Ala Arg Ala Ala
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      spacer sequence

<400> SEQUENCE: 5

Ala Arg Ser Leu
1

<210> SEQ ID NO 6
<211> LENGTH: 2
<212> TYPE: PRT
<213> ORGANISM: Artificial Sequence
<220> FEATURE:
<223> OTHER INFORMATION: Description of Artificial Sequence: Synthetic
      spacer sequence

<400> SEQUENCE: 6

Pro Ile
1

<210> SEQ ID NO 7
<211> LENGTH: 2
<212> TYPE: PRT
<213> ORGANISM: Artificial Sequence
<220> FEATURE:
<223> OTHER INFORMATION: Description of Artificial Sequence: Synthetic
      spacer sequence

<400> SEQUENCE: 7

Asn Pro
1

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      spacer sequence

<400> SEQUENCE: 8

Leu Val Gly
1

<210> SEQ ID NO 9
<211> LENGTH: 705
<212> TYPE: DNA
<213> ORGANISM: Artificial Sequence
```

<220> FEATURE:
<223> OTHER INFORMATION: Description of Artificial Sequence: Synthetic
    nucleic acid sequence encoding a recombinant light chain
    polypeptide
<220> FEATURE:
<221> NAME/KEY: CDS
<222> LOCATION: (1)..(702)

<400> SEQUENCE: 9

```
gac atc cag atg acc cag tct cca tcc tcc ctg tcc gca tct gta gga      48
Asp Ile Gln Met Thr Gln Ser Pro Ser Ser Leu Ser Ala Ser Val Gly
1               5                   10                  15 gac aga gtc acc ctc act tgc cgg gca agt cag ggc gtt aga aat gct      96
Asp Arg Val Thr Leu Thr Cys Arg Ala Ser Gln Gly Val Arg Asn Ala
            20                  25                  30 tta gtc tgg tat cag cag aaa cca gga aaa gcc cct gag cgc ctg atc     144
Leu Val Trp Tyr Gln Gln Lys Pro Gly Lys Ala Pro Glu Arg Leu Ile
        35                  40                  45 tac gct gca tcc att ttg caa agt ggg gtc cca tca agg ttc agc ggc     192
Tyr Ala Ala Ser Ile Leu Gln Ser Gly Val Pro Ser Arg Phe Ser Gly
    50                  55                  60 agt gga tct ggg aca gaa ttc act ctc aca atc ggc ggc ctg cag cct     240
Ser Gly Ser Gly Thr Glu Phe Thr Leu Thr Ile Gly Gly Leu Gln Pro
65                  70                  75                  80 gaa gat ttc gca act tat tac tgt cta cag cat aat agt tac ccg tgg     288
Glu Asp Phe Ala Thr Tyr Tyr Cys Leu Gln His Asn Ser Tyr Pro Trp
                85                  90                  95 acg ttc ggc caa ggg acc aag gtg gaa atc aag cga act gtg gct gca     336
Thr Phe Gly Gln Gly Thr Lys Val Glu Ile Lys Arg Thr Val Ala Ala
            100                 105                 110 cca tct gtc ttc atc ttc ccg cca tcc gat gag cag ttg aaa tct gga     384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tgt gcg aga tca ctg att gaa ggg ccg acg ctg     672
Phe Asn Arg Gly Glu Cys Ala Arg Ser Leu Ile Glu Gly Pro Thr Leu
    210                 215                 220 cgg caa tgg ctg gcg gcg cgc gcg ccc atc taa                         705
Arg Gln Trp Leu Ala Ala Arg Ala Pro Ile
225                 230
```

<210> SEQ ID NO 10
<211> LENGTH: 234
<212> TYPE: PRT
<213> ORGANISM: Artificial Sequence
<220> FEATURE:
<223> OTHER INFORMATION: Description of Artificial Sequence: Synthetic
    construct -continued

<400> SEQUENCE: 10

Asp Ile Gln Met Thr Gln Ser Pro Ser Leu Ser Ala Ser Val Gly
1               5                   10                  15

Asp Arg Val Thr Leu Thr Cys Arg Ala Ser Gln Gly Val Arg Asn Ala
            20                  25                  30

Leu Val Trp Tyr Gln Gln Lys Pro Gly Lys Ala Pro Glu Arg Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Glu Phe Thr Leu Thr Ile Gly Gly Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Arg Ser Leu Ile Glu Gly Pro Thr Leu
    210                 215                 220

Arg Gln Trp Leu Ala Ala Arg Ala Pro Ile
225                 230

<210> SEQ ID NO 11
<211> LENGTH: 1389
<212> TYPE: DNA
<213> ORGANISM: Artificial Sequence
<220> FEATURE:
<223> OTHER INFORMATION: Description of Artificial Sequence: Synthetic
      nucleic acid sequence encoding a recombinant heavy chain
      polypeptide
<220> FEATURE:
<221> NAME/KEY: CDS
<222> LOCATION: (1)..(1383)

<400> SEQUENCE: 11 cag gtc cag ctt gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtt tcc tgc aag gcc tct gga tac acc ttc act tac tat      96
Ser Val Lys Val Ser Cys Lys Ala Ser Gly Tyr Thr Phe Thr Tyr Tyr
            20                  25                  30 gct atg cat tgg gtg cgc cag gcc ccc gga caa aga cct gag tgg atg     144
Ala Met His Trp Val Arg Gln Ala Pro Gly Gln Arg Pro Glu Trp Met
        35                  40                  45 gga tgg atc aac ggt ggc gat gga aaa aca aaa tat gca cag aag ttc     192
Gly Trp Ile Asn Gly Gly Asp Gly Lys Thr Lys Tyr Ala Gln Lys Phe
    50                  55                  60 cag ggc aga ctc gcc att acc agg gac aca tcc gcg agg acc gcc tac     240

```
                                                -continued

Gln Gly Arg Leu Ala Ile Thr Arg Asp Thr Ser Ala Arg Thr Ala Tyr
      65                  70                  75                  80 atg gag ctg atc agc ctg aca tct gaa gac acg gct gtg tat tac tgt       288
Met Glu Leu Ile Ser Leu Thr Ser Glu Asp Thr Ala Val Tyr Tyr Cys
                     85                  90                  95 gca aaa ggg gcc gag atg acc gtg ggc tcc tgg ggc ccg gga acc ctg       336
Ala Lys Gly Ala Glu Met Thr Val Gly Ser Trp Gly Pro Gly Thr Leu
                100                 105                 110 gtc acc gtc tcc tca gcc tcc acc aag ggc cca tcc gtc ttc ccc ctg       384
Val Thr Val Ser Ser Ala Ser Thr Lys Gly Pro Ser Val Phe Pro Leu
            115                 120                 125 gcg ccc tgc tcc agg agc acc tcc gag agc aca gcc gcc ctg ggc tgc       432
Ala Pro Cys Ser Arg Ser Thr Ser Glu Ser Thr Ala Ala Leu Gly Cys
        130                 135                 140 ctg gtc aag gac tac ttc ccc gaa ccg gtg acg gtg tcg tgg aac tca       480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc aac       576
Ser Gly Leu Tyr Ser Leu Ser Ser Val Val Thr Val Pro Ser Ser Asn
            180                 185                 190 ttc ggc acc cag acc tac acc tgc aac gta gat cac aag ccc agc aac       624
Phe Gly Thr Gln Thr Tyr Thr Cys Asn Val Asp His Lys Pro Ser Asn
        195                 200                 205 acc aag gtg gac aag aca gtt gag cgc aaa tgt tgt gtc gag tgc cca       672
Thr Lys Val Asp Lys Thr Val Glu Arg Lys Cys Cys Val Glu Cys Pro
    210                 215                 220 ccg tgc cca gca cca cct gtg gca aat ccg atc gaa ggc cca acc ctg       720
Pro Cys Pro Ala Pro Pro Val Ala Asn Pro Ile Glu Gly Pro Thr Leu
225                 230                 235                 240 cgc cag tgg ctg gct gct cgc gct cgt ggg gga ccg tca gtc ttc ctc       768
Arg Gln Trp Leu Ala Ala Arg Ala Arg Gly Gly Pro Ser Val Phe Leu
                245                 250                 255 ttc ccc cca aaa ccc aag gac acc ctc atg atc tcc cgg acc cct gag       816
Phe Pro Pro Lys Pro Lys Asp Thr Leu Met Ile Ser Arg Thr Pro Glu
            260                 265                 270 gtc acg tgc gtg gtg gtg gac gtg agc cag gaa gac ccc gag gtc cag       864
Val Thr Cys Val Val Val Asp Val Ser Gln Glu Asp Pro Glu Val Gln
        275                 280                 285 ttc aac tgg tac gtg gat ggc gtg gag gtg cat aat gcc aag aca aag       912
Phe Asn Trp Tyr Val Asp Gly Val Glu Val His Asn Ala Lys Thr Lys
    290                 295                 300 ccg cgg gag gag cag ttc aac agc acg tac cgt gtg gtc agc gtc ctc       960
Pro Arg Glu Glu Gln Phe Asn Ser Thr Tyr Arg Val Val Ser Val Leu
305                 310                 315                 320 acc gtc ctg cac cag gac tgg ctg aac ggc aag gag tac aag tgc aag      1008
Thr Val Leu His Gln Asp Trp Leu Asn Gly Lys Glu Tyr Lys Cys Lys
                325                 330                 335 gtc tcc aac aaa ggc ctc ccg tcc tcc atc gag aaa acc atc tcc aaa      1056
Val Ser Asn Lys Gly Leu Pro Ser Ser Ile Glu Lys Thr Ile Ser Lys
            340                 345                 350 gcc aaa ggg cag ccc cga gag cca cag gtg tac acc ctg ccc cca tcc      1104
Ala Lys Gly Gln Pro Arg Glu Pro Gln Val Tyr Thr Leu Pro Pro Ser
        355                 360                 365 cag gag gag atg acc aag aac cag gtc agc ctg acc tgc ctg gtc aaa      1152
Gln Glu Glu Met Thr Lys Asn Gln Val Ser Leu Thr Cys Leu Val Lys
    370                 375                 380
```

```
ggc ttc tac ccc agc gac atc gcc gtg gag tgg gag agc aat ggg cag    1200
Gly Phe Tyr Pro Ser Asp Ile Ala Val Glu Trp Glu Ser Asn Gly Gln
385                 390                 395                 400 ccg gag aac aac tac aag acc acg cct ccc gtg ctg gac tcc gac ggc    1248
Pro Glu Asn Asn Tyr Lys Thr Thr Pro Pro Val Leu Asp Ser Asp Gly
                405                 410                 415 tcc ttc ttc ctc tac agc agg cta acc gtg gac aag agc agg tgg cag    1296
Ser Phe Phe Leu Tyr Ser Arg Leu Thr Val Asp Lys Ser Arg Trp Gln
            420                 425                 430 gag ggg aat gtc ttc tca tgc tcc gtg atg cat gag gct ctg cac aac    1344
Glu Gly Asn Val Phe Ser Cys Ser Val Met His Glu Ala Leu His Asn
        435                 440                 445 cac tac aca cag aag agc ctc tcc ctg tct ctg ggt aaa tgatga         1389
His Tyr Thr Gln Lys Ser Leu Ser Leu Ser Leu Gly Lys
    450                 455                 460

<210> SEQ ID NO 12
<211> LENGTH: 461
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Ala Met His Trp Val Arg Gln Ala Pro Gly Gln Arg Pro Glu Trp Met
        35                  40                  45

Gly Trp Ile Asn Gly Gly Asp Gly Lys Thr Lys Tyr Ala Gln Lys Phe
    50                  55                  60

Gln Gly Arg Leu Ala Ile Thr Arg Asp Thr Ser Ala Arg Thr Ala Tyr
65                  70                  75                  80

Met Glu Leu Ile Ser Leu Thr Ser Glu Asp Thr Ala Val Tyr Tyr Cys
                85                  90                  95

Ala Lys Gly Ala Glu Met Thr Val Gly Ser Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220
```

Pro Cys Pro Ala Pro Pro Val Ala Asn Pro Ile Glu Gly Pro Thr Leu
225                 230                 235                 240

Arg Gln Trp Leu Ala Ala Arg Ala Arg Gly Gly Pro Ser Val Phe Leu
            245                 250                 255

Phe Pro Pro Lys Pro Lys Asp Thr Leu Met Ile Ser Arg Thr Pro Glu
        260                 265                 270

Val Thr Cys Val Val Val Asp Val Ser Gln Glu Asp Pro Glu Val Gln
            275                 280                 285

Phe Asn Trp Tyr Val Asp Gly Val Glu Val His Asn Ala Lys Thr Lys
        290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Gly Leu Pro Ser Ser Ile Glu Lys Thr Ile Ser Lys
        340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Arg Leu Thr Val Asp Lys Ser Arg Trp Gln
        420                 425                 430

Glu Gly Asn Val Phe Ser Cys Ser Val Met His Glu Ala Leu His Asn
        435                 440                 445

His Tyr Thr Gln Lys Ser Leu Ser Leu Ser Leu Gly Lys
        450                 455                 460

<210> SEQ ID NO 13
<211> LENGTH: 7
<212> TYPE: PRT
<213> ORGANISM: Homo sapiens

<400> SEQUENCE: 13

Glu Gln Trp Lys Ser His Lys
1               5

<210> SEQ ID NO 14
<211> LENGTH: 5
<212> TYPE: PRT
<213> ORGANISM: Homo sapiens

<400> SEQUENCE: 14

Pro Ala Glu Cys Ser
1               5

<210> SEQ ID NO 15
<211> LENGTH: 7
<212> TYPE: PRT
<213> ORGANISM: Homo sapiens

<400> SEQUENCE: 15

Ser Asp Glu Gln Leu Lys Ser
1               5

```
<210> SEQ ID NO 16
<211> LENGTH: 6
<212> TYPE: PRT
<213> ORGANISM: Homo sapiens

<400> SEQUENCE: 16

Ala Asp Tyr Glu Lys His
1               5
```